(12) United States Patent
Yan

(10) Patent No.: US 11,168,320 B2
(45) Date of Patent: Nov. 9, 2021

(54) STRUCTURE ASSISTED DIRECTED EVOLUTION OF MULTIVALENT APTAMERS

(71) Applicant: Arizona Board of Regents on behalf of Arizona State University, Scottsdale, AZ (US)

(72) Inventor: Hao Yan, Chandler, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 172 days.

(21) Appl. No.: 15/673,017

(22) Filed: Aug. 9, 2017

(65) Prior Publication Data

US 2018/0044663 A1 Feb. 15, 2018

Related U.S. Application Data

(60) Provisional application No. 62/372,680, filed on Aug. 9, 2016.

(51) Int. Cl.
*C12N 15/10* (2006.01)
*C12N 15/115* (2010.01)

(52) U.S. Cl.
CPC ..... *C12N 15/1058* (2013.01); *C12N 15/1013* (2013.01); *C12N 15/115* (2013.01); *C12N 2310/16* (2013.01); *C12N 2320/13* (2013.01)

(58) Field of Classification Search
CPC ............ C12N 15/1058; C12N 15/1013; C12N 15/115; C12N 2320/13
See application file for complete search history.

(56) References Cited

U.S. PATENT DOCUMENTS

| | | | | |
|---|---|---|---|---|
| 8,105,982 B2* | 1/2012 | Doyle | ............... | C12N 15/115 506/4 |
| 8,129,516 B1* | 3/2012 | Leontis | ............... | C12N 15/111 536/24.1 |
| 8,440,811 B2* | 5/2013 | Chang | ............... | A61K 31/711 536/23.1 |
| 8,552,167 B2 | 10/2013 | Chang et al. | | |
| 8,685,894 B2 | 4/2014 | Chaput et al. | | |
| 9,202,867 B2 | 12/2015 | Yan et al. | | |
| 9,732,273 B2 | 8/2017 | Yan et al. | | |
| 9,944,923 B2 | 4/2018 | Blattman et al. | | |
| 10,189,874 B2 | 1/2019 | Han et al. | | |
| 2009/0018028 A1 | 1/2009 | Lindsay et al. | | |
| 2010/0009868 A1 | 1/2010 | Yan et al. | | |
| 2014/0031416 A1 | 1/2014 | Chang et al. | | |
| 2014/0220655 A1* | 8/2014 | Sun | ............... | C12N 9/98 435/187 |
| 2014/0221253 A1* | 8/2014 | Johnston | ............ | C07K 16/2881 506/16 |
| 2015/0004193 A1 | 1/2015 | Chang et al. | | |
| 2015/0218204 A1* | 8/2015 | Yin | ............... | C07H 21/04 536/23.1 |
| 2016/0145679 A1 | 5/2016 | Yan et al. | | |
| 2018/0016569 A1 | 1/2018 | Fu et al. | | |
| 2018/0216102 A1 | 8/2018 | Blattman et al. | | |
| 2019/0144491 A1 | 5/2019 | Han et al. | | |
| 2019/0240248 A1 | 8/2019 | Yan et al. | | |

FOREIGN PATENT DOCUMENTS

| | | | |
|---|---|---|---|
| WO | 2006124089 A1 | 11/2006 | |
| WO | 2007139849 A2 | 12/2007 | |
| WO | 2008033848 A2 | 3/2008 | |
| WO | 2010040091 A1 | 4/2010 | |
| WO | 2010060030 A1 | 5/2010 | |
| WO | 2011049750 A1 | 4/2011 | |
| WO | 2013052541 A2 | 4/2013 | |
| WO | 2013119676 A1 | 8/2013 | |
| WO | 2014134338 A1 | 9/2014 | |
| WO | 2014200933 A1 | 12/2014 | |
| WO | 2015130805 A1 | 9/2015 | |
| WO | WO-2016144755 A1 * | 9/2016 | ............. C07H 21/04 |
| WO | 2018165465 A1 | 9/2018 | |
| WO | 2019109707 A1 | 6/2019 | |
| WO | 2019140140 A1 | 7/2019 | |
| WO | 2019147308 A2 | 8/2019 | |
| WO | 2019147309 A2 | 8/2019 | |

OTHER PUBLICATIONS

Marimuthu et al.( Analyst 137.6 (2012): 1307-1315 ) (Year: 2012).*
Shen et al. (Journal of the American Chemical Society 126.6 (2004): 1666-1674.). (Year: 2004).*
Li et al. (Journal of the American Chemical Society 118.26 (1996): 6131-6140). (Year: 1996).*
Lin et al.( Angewandte Chemie International Edition 45.32 (2006): 5296-5301.). (Year: 2006).*
Lin et al. (Proceedings of the National Academy of Sciences 105.46 (2008): 17626-17631.) (Year: 2008).*
Lin et al. (Angewandte Chemie International Edition 45.45 (2006): 7537-7539) (Year: 2006).*
Mencin (Thesis: In vitro selection of DNA aptamers for proteins immobilized on magnetic beads and monitoring of ssDNA pool evolution. Diss. Univerza v Novi Gorici, Fakulteta za podiplomski študij, 2015) (Year: 2015).*
Ahmad et al. ("Selection is more intelligent than design: improving the affinity of a bivalent ligand through directed evolution." Nucleic acids research 40.22 (2012): 11777-11783). (Year: 2012).*
Ahmad 2012 supplementary materials (Year: 2012).*

(Continued)

*Primary Examiner* — Sahana S Kaup

(74) *Attorney, Agent, or Firm* — Duane Morris LLP

(57) ABSTRACT

Provided herein are methods and systems for structure-assisted evolution of multivalent aptamers using a single stranded DNA or single-stranded RNA nanostructure as a structural support. Also provided herein are methods for constructing ssDNA or ssRNA nanostructures as structural supports suitable for structure-assisted evolution of multivalent aptamers.

20 Claims, 15 Drawing Sheets

Specification includes a Sequence Listing.

(56) References Cited

OTHER PUBLICATIONS

Pinheiro, A. et al., "Challenges and opportunities for structural DNA nanotechnology", Nature Nanotechnology, Nov. 2011, vol. 6, No. 12, pp. 763-772 <DOI:10.1038/nnano.2011.187>.

Rinker, S. et al., "Self-assembled DNA nanostructures for distance dependent multivalent ligand-protein binding", National Nanotechnology, Jul. 2008, vol. 3, No. 7, pp. 418-422 <DOI:10.1038/nnano.2008.164>.

Rodgers, P., "Nanoelectronics: Single File", Nature Nanotechnology, Jun. 2006 <DOI:10.1038/nnano.2006.5>.

Rothemund, P. et al., "Algorithmic self-assembly of DNA Sierpinski triangles", PLoS Biology, Dec. 2004, vol. 2, No. 12, article e424, pp. 2041-2053 <DOI:10.1371/journal.pbio.0020424>.

Rothemund, P. et al., "Folding DNA to create nanoscale shapes and patterns", Nature, Mar. 2006, vol. 440, pp. 297-302 <DOI:0.1038/nature04586>.

Sacca, B. et al., "Orthogonal Protein Decoration of DNA Origami", Angewandte Chemie, Dec. 2010, vol. 49, pp. 9378-9383 <DOI:10.1002/anie.201005931>.

Schmidt, G. et al., "Properties of polymer-nanoparticle composites", Current Opinion in Colloid and Interface Science, Mar. 2003, vol. 8, No. 1, pp. 103-108 <DOI:10.1016/S1359-0294Ž03.00008-6>.

Schreiber, R. et al., "Hierarchical assembly of metal nanoparticles, quantum dots and organic dyes using DNA origami scaffolds", Nature Nanotechnology, Jan. 2014, vol. 9, No. 1, pp. 74-78 <DOI:10.1038/nnano.2013.253>.

Seeman, N. et al., "Nanomaterials Based on DNA", Annual Review of Biochemistry, Mar. 2010, vol. 79, pp. 65-87 <DOI:10.1146/annurev-biochem-060308-102244>.

Seeman, N. et al., "Nucleic Acid Junctions and Lattices", Journal of Theoretical Biology, Nov. 1982, vol. 99, No. 2, pp. 237-247 <DOI:10.1016/0022-5193(82)90002-9>.

Seeman, N. et al., "Optimal-Design of Immobile and Semi-Mobile Nucleic-Acid Junctions", Biophysical Journal, 1982, vol. 37, pp. A93.

Selmi, D. et al., "DNA-Templated Protein Arrays for Single-Molecule Imaging", Nano Letters, Feb. 2011, vol. 11, No. 2, pp. 657-660 <DOI:10.1021/nl1037769>.

Service, R., "DNA Nanotechnology Grows Up", Science, Jun. 2011, vol. 332, No. 6034, pp. 1140-1143 <DOI:10.1126/science.332.6034.1140>.

Sharma, J. et al., "Control of Self-Assembly of DNA Tubules Through Integration of Gold Nanoparticles", Science, Jan. 2009, vol. 323, No. 5910, pp. 112-116 <DOI:10.1126/science.1165831>.

Sharma, J. et al., "DNA-Templated Self-Assembly of Two-Dimensional and Periodical Gold Nanoparticle Arrays", Angewandte Chemie, Jan. 2006, vol. 45, No. 5, pp. 730-735 <DOI:10.1002/anie.200503208>.

Shen, Z. et al., "Paranemic Crossover DNA: A Generalized Holliday Structure with Applications in Nanotechnology", Journal of the American Chemical Society, Jan. 2004, vol. 126, No. 6, pp. 1666-1674 <DOI:10.1021/ja038381e>.

Shukla, G. et al., "A Boost for the Emerging Field of RNA Nanotechnology", American Chemical Society Nanotechnology, May 2011, vol. 5, No. 5, pp. 3405-3418 <DOI:10.1021/nn200989r>.

Soh, T. et al., "Selection is more intelligent than design: improving the affinity of a bivalent ligand through directed evolution", Nucleic Acids Research, Dec. 2012, vol. 40, No. 22, pp. 11777-11783 <DOI:10.1093/nar/gks899>.

Stephanopoulos, N. et al., "Immobilization and One-Dimensional Arrangement of Virus Capsids with Nanoscale Precision using DNA Origami", Nano Letters, Jul. 2010, vol. 10, No. 7, pp. 2714-2720 <DOI:10.1021/nl1018468>.

Sun, Y. et al., "Shape-Controlled Synthesis of Gold and Silver Nanoparticles", Science Report, Dec. 2002, vol. 298, No. 5601, pp. 2176-2179 <DOI:10.1126/science.1077229>.

Urban, A. et al., "Laser Printing Single Gold Nanoparticles", Nano Letters, Oct. 2010, vol. 10, No. 12, pp. 4794-4798 <DOI:10.1021/nl1030425>.

Verma, S. et al., "Modified oligonucleotides: synthesis and strategy for users", Annual Review of Biochemistry, 1998, vol. 67, pp. 99-134 <DOI:10.1146/annurev.biochem.67.1.99>.

Wacaser, B. et al., "Chemomechanical surface patterning and fuctionalization of silicon sufaces using an atomic force microscope", Applied Physics Letters, Feb. 2003, vol. 82, No. 5, pp. 808-810 <DOI:10.1063/1.1535267>.

Wang, D. et al., "Thermochemical Nanolithography of Multifunctional Nanotemplates for Assembling Nano-Objects", Advanced Functional Materials, Dec. 2009, vol. 19, pp. 3696-3702 <DOI:10.1002/adfm.200901057>.

Wang, X. et al., "Fabrication of ultralong and electrically uniform single-walled carbon nanotubes on clean substrates", Nano Letters, Sep. 2009, vol. 9, No. 9, pp. 3137-3141 <DOI:10.1021/nl901260b>.

Watson, J. et al., "Molecular Structure of Nucleic Acids: A Structure for Deoxyribose Nucleic Acid", Nature, Apr. 1953, vol. 171, No. 4356, pp. 737.

Wei, B. et al., "Complex Shapes Self-Assembled from Single-Stranded DNA Tiles", Nature, May 2012, vol. 485, No. 7400, pp. 623-626 <DOI:10.1038/nature11075>.

Whitesides, G. et al., "Self-Assembly at All Scales", Science Reports, Mar. 2002, vol. 295, No. 5564, pp. 2481-2421 <DOI:10.1126/science.1070821>.

Williams, B. et al., "Self-assembled peptide nanoarrays: an approach to studying protein-protein interactions", Angewandte Chemie, 2007, vol. 46, No. 17, pp. 3051-3054 <DOI:10.1002/anie.200603919>.

Williams, S. et al., "Tiamat: A Three-Dimensional Editing Tool for Complex DNA Structures", DNA Computing, 2009, vol. 5347, pp. 90-101 <DOI:10.1007/978-3-642-03076-5_8>.

Wilson, R. et al., "Single-Step Selection of Bivalent Aptamers validated by Comparison with SELEX Using High-Throughput Sequencing", PLoS One, Jun. 2014, vol. 9, No. 6, article e100572, 11 pages <DOI:10.1371/journal.pone.0100572>.

Winfree, E. et al., "Design and Self-Assembly of Two-Dimensional DNA Crystals", Nature, Aug. 1998, vol. 394, No. 6693, pp. 539-544 <DOI:10.1038/28998>.

Wollman, A. et al., "Transport and self-organization across different length scales powered by motor proteins and programmed by DNA", Nature Nanotechnology, Jan. 2014, vol. 9, pp. 44-47 <DOI:10.1038/NNANO.2013.230>.

Yakovchuk, P. et al., "Base-stacking and base-pairing contributions into thermal stability of the DNA double helix", Nucleic Acids Research, Jan. 2006, vol. 34, No. 2, pp. 564-574 <DOI:10.1093/nar/gkj454>.

Yan, H. et al., "DNA-templated self-assembly of protein arrays and highly conductive nanowires", Science Reports, Sep. 2003, vol. 301, No. 5641, pp. 1882-1884 <DOI:10.1126/science.1089389>.

Yin, P. et al., "Programming DNA Tube Circumferences", Science, Aug. 2008, vol. 321, No. 5890, pp. 824-826 <DOI:10.1126/science.1157312>.

Zadegan, R. et al., "Structural DNA Nanotechnology: From Design and Application", International Journal of Molecular Science, Jun. 2012, vol. 13, No. 6, pp. 7149-7162 <DOI:10.3390/ijms13067149>.

Zhang, F. et al., "Complex Archimedean Tiling Self-Assembled from DNA Nanostructures", Journal of the American Chemical Society, May 2013, vol. 135, No. 20, pp. 7458-7461 <DGI:10.1021/ja4035957>.

Zhang, F. et al., "Structural DNA Nanotechnology: State of the Art and Future Perspective", Journal of the American Chemical Society, Jul. 2014, vol. 136, No. 32, pp. 11198-11211 <DOI:10.1021/ja505101a>.

Zhang, X. et al., "Paranemic Cohesion of Topologically-Closed DNA Molecules", Journal of the American Chemical Society, Oct. 2002, vol. 124, No. 44, pp. 12940-12941 <DOI:10.1021/ja026973b>.

Zheng, J. et al., "From molecular to macroscopic via the rational design of a self-assembled 3D DNA crystal", Nature, Sep. 2009, vol. 461, No. 7260, pp. 74-77 <DOI:10.1038/nature08274>.

Zheng, J. et al., "Two-dimensional Nanoparticle Arrays Show the Organizational Power of Robust DNA Motifs", Nano Letters, Jul. 2006, vol. 6, No. 7, pp. 1502-1504 <DOI:10.1021/nl060994c>.

(56) References Cited

OTHER PUBLICATIONS

Zhou, Y. et al., "DNA Nanoscaffold-Assisted Selection of Femtomolar Bivalent Aptamers for Human α-Thrombin with Potent Anticoagulant Activity", ChemBioChem, May 2019 [available online ahead of print], <DOI:10.1002/cbic.201900265>.

Aldaye, F. et al., "Assembling Materials with DNA as the Guide", Science Reports, Sep. 2008, vol. 321, No. 5897, pp. 1795-1799 <DOI:10.1126/science.1154533>.

Ball, P., "Small Problems" Nature, Mar. 1993, vol. 362, pp. 123.

Chhabra, R. et al., "Distance-dependent interactions between gold nanoparticles and fluorescent molecules with DNA as tunable spacers", Nanotechnology, Oct. 2009, vol. 20, No. 48, article 485201, 11 pages <DOI:10.1088/0957-4484/20/48/485201>.

Chhabra, R. et al., "Spatially Addressable Multiprotein Nanoarrays Templated by Aptamer-Tagged DNA Nanoarchitectures", Journal of the American Chemical Society, Aug. 2007, vol. 129, No. 34, pp. 10304-10305 <DOI:10.1021/ja072410u>.

Chou, L. et al., "DNA assembly of nanoparticle superstructures for controlled biological delivery and elimination", Nature Nanotechnology, Feb. 2014 (available online Jan. 2014), vol. 9, No. 2, pp. 148-155 <DOI:10.1038%2Fnnano.2013.309>.

Deng, Z. et al., "Robust DNA-Functionalized Core/Shell Quantum Dots with Fluorescent Emission Spanning from UV-vis to Near-IR and Compatible with DNA-Directed Self-Assembly", Journal of the American Chemical Society, Oct. 2012, vol. 134, No. 42, pp. 17424-17427 <DOI:10.1021/ja3081023>.

Derr, N. et al., "Tug-of-War in Motor Protein Ensembles Revealed with a Programmable DNA Origami Scaffold", Science Reports, Nov. 2012, vol. 338, No. 6107, pp. 662-665 <DOI:10.1126/science.1226734>.

Dietz, H. et al., "Folding DNA into Twisted and Curved Nanoscale Shapes", Science, Aug. 2009, vol. 325, No. 5941, pp. 725-730 <DOI:10.1126/science.1174251>.

Douglas, S. et al., "Self-assembly of DNA into nanoscale three-dimensional shapes", Nature, May 2009, vol. 459, No. 7245, pp. 414-418 <DOI:10.1038/nature08016>.

Ducani, C. et al., "Enzymatic production of 'monoclonal stoichiometric' single-stranded DNA oligonucleotides", Nature Methods, Jul. 2013, vol. 10, No. 7, pp. 647-652 <DOI:10.1038/nmeth.2503>.

Elbaz, J. et al., "Powering the programmed nanostructure and function of gold nanoparticles with catenated DNA machines", Nature Communications, Jun. 2013, vol. 4, article 2000, 7 pages <DOI:10.1038/ncomms3000>.

Fu, J. et al., "Multi-enzyme complexes on DNA scaffolds capable of substrate channelling with an artificial swinging arm", Nature Nanotechnology, May 2014, vol. 9, pp. 531-536 <DOI:10.1038/nnano.2014.100>.

Geary, C. et al., "A single-stranded architecture for contranscriptional folding of RNA nanostructures", Science, Aug. 2014, vol. 345, No. 6198, pp. 799-804 <DOI:10.1126/science.1253920>.

Gibson, D. et al., "Enzymatic assembly of DNA molecules up to several hundred kilobases", Nature Methods, May 2009, vol. 6, No. 5, pp. 343-345 <DOI:10.1038/NMETH.1318>.

Guo, P., "The Emerging Field of RNA Nanotechnology", Nature Nanotechnology, Dec. 2010, vol. 5, No. 12, pp. 833-842 <DOI:10.1038/nnano.2010.231>.

Han, D. et al., "DNA Gridiron Nanostructures Based on Four-Arm Junctions", Science Reports, Mar. 2013, vol. 339, No. 6126, pp. 1412-1415 <DOI:10.1126/science.1232252>.

Han, D. et al., "DNA Origami with Complex Curvatures in Three-Dimensional Space", Science Reports, Apr. 2011, vol. 332, No. 6027, pp. 342-346 <DOI:10.1126/science.1202998>.

Han, D. et al., "Folding and cutting DNA into reconfigurable topological nanostructures", Nature Nanotechnology, Oct. 2010, vol. 5, No. 10, pp. 712-717 <DOI:10.1038/nnano.2010.193>.

He, Y. et al., "Highly Connected Two-Dimensional Crystals of DNA Six-Point-Stars", Journal of the American Chemical Society, Nov. 2006, vol. 128, No. 50, pp. 15978-15979 <DOI:10.1021/ja0665141>.

He, Y. et al., "Self-Assembly of Hexagonal DNA Two-Dimensional (2D) Arrays", Journal of the American Chemical Society, Aug. 2005, vol. 127, No. 35, pp. 12202-12203 <DOI:10.1021/ja0541938>.

Hemphill, J. et al., "DNA Computation in Mammalian Cells: MicroRNA Logic Operations", Journal of the American Chemical Society, Jun. 2013, vol. 135, No. 28, pp. 10512-10518 <DOI:10.1021/ja404350s>.

Ke, Y. et al., "Self-Assembled Water-Soluble Nucleic Acid Probe Tiles for Label-Free RNA Hybridization Assays", Science, Jan. 2008, vol. 319, No. 5860, pp. 180-183 <DOI:10.1126/science.1150082>.

Ke, Y. et al., "Three-Dimensional Structures Self-Assembled from DNA Bricks", Science Reports, Nov. 2012, vol. 338, No. 6111, pp. 1177-1183 <DOI:10.1126/science.1227268>.

King, N. et al., "Computational Design of Self-Assembling Protein Nanomaterials with Atomic Level Accuracy", Science Reports, Jun. 2012, vol. 336, No. 6085, pp. 1171-1174 <DOI:10.1126/science.1219364>.

Kuzyk, A. et al., "DNA-based self-assembly of plasmonic nanostructures with tailored optical response", Nature, Mar. 2012, vol. 483, No. 7389, pp. 311-314 <DOI:10.1038/nature10889>.

Lackenby, M. et al., "The crossing number of composite knots", Journal of Topology, 2009, vol. 2, pp. 747-768 <DOI:10.1112/jtopol/jtp028>.

Lai, Y-T. et al., "Structure of a 16-nm Cage Designed by Using Protein Oligomers", Science Reports, Jun. 2012, vol. 336, No. 6085, pp. 1129 <DOI:10.1126/science.1219351>.

Lee, H. et al., "Rate and molecular spectrum of spontaneous mutations in the bacterium *Escherichia coli* as determined by whole-genome sequencing", Proceedings of the National Academy of the United States of America, Oct. 2012, vol. 109, No. 41, pp. E2774-E2783 <DOI:10.1073/pnas.1210309109>.

Li, H. et al., "Nanofabrication by DNA self-assembly", Science Direct, May 2009, vol. 12, No. 5, pp. 24-32 <DOI:10.1016/S1369-7021(09)70157-9>.

Lin, C. et al., "In vivo cloning of artificial DNA nanostructures", Proceedings of the National Academy of Sciences of the United States of America, Nov. 2008, vol. 105, No. 46, pp. 17626-17631 <DOI:10.1073pnas.0805416105>.

Lin, C. et al., "Rolling-Circle Amplification of a DNA Nanojunction", Angewandte Chemie, Nov. 2006, vol. 45, No. 45, pp. 7537-7539 <DOI:10.1002/anie.200602113>.

Liu, J. et al., "Stabilization of Colloidal Suspensions by Means of Highly Charged Nanoparticles" Physical Review Letters, Dec. 2004, vol. 93, No. 24, article 247802, 4 pages <DOI:10.1103/PhysRevLett.93.247802>.

Liu, M. et al., "A DNA tweezer-actuated enzyme nanoreactor", Nature Communications, Jul. 2013, vol. 4, article 2127, 5 pages <DOI:10.1038/ncomms3127>.

Liu, Y. et al., "Self-Assembly of Symmetric Finite-Size DNA Nanoarrays", Journal of the American Chemical Society, Nov. 2005, vol. 127, No. 49, pp. 17140-17141 <DOI:10.1021/ja055614o>.

Long, N. et al., "Synthesis and Characterization of Fe-Based Metal and Oxide Based Nanoparticles: Discoveries and Research Highlights of Potential Applications in Biology and Medicine", Recent Patents on Nanotechnology, Jan. 2014, vol. 8, No. 1, pp. 52-61 <DOI:10.2174/187221050766613111718300 8>.

Loria, A. et al., "Modular construction for function of a ribonucleoprotein enzyme: the catalytic domain of Bacillus Subtilis Rnase P complexed with B. subtilis Rnase P protein", Nucleic Acids Research, May 2001, vol. 29, No. 9, 1892-1897 <DOI:10.1093/nar/29.9.1892>.

Lund, K. et al., "Molecular robots guided by prescriptive landscapes", Nature, May 2010, vol. 465, pp. 206-210 <DOI:10.1038/nature09012>.

Malo, J. et al., "Engineering a 2D protein-DNA crystal", Angewandte Chemie, May 2005, vol. 44, No. 20, pp. 3057-3061 <DOI:10.1002/anie.200463027>.

Mammen, M. et al., "Polyvalent Interactions in Biological Systems: Implications for Design and Use of Multivalent Ligands and Inhibitors", Angewandte Chemie, Nov. 1998, vol. 37, No. 20, pp. 2754-2794 <DOI:10.1002/(SICI)1521-3773(19981102)37:20<2754::AID-ANIE2754>3.0.CO;2-3>.

(56) References Cited

OTHER PUBLICATIONS

Mandelkern, M. et al., "The dimensions of DNA in solution", Journal of Molecular Biology, Oct. 1981, vol. 152, No. 1, pp. 153-161 <DOI:10.1016/0022-2836(81)90099-1>.

Mao, C. et al., "Assembly of Borromean rings from DNA", Nature, Mar. 1997, vol. 386, No. 6621, pp. 137-138 <DOI:10.1038/386137b0>.

Martel, R. et al., "Ambipolar Electrical Transport in Semiconducting Single-Wall Carbon Nanotubes", Physical Review Letters, Dec. 2001, vol. 87, No. 25, article 256805, 4 pages <DOI:10.1103/PhysRevLett.87.256805>.

Maune, H. et al., "Self-assembly of carbon nanotubes into two-dimensional geometries using DNA origami templates", Nature Nanotechnology, Jan. 2010, vol. 5, No. 1, pp. 61-66 <DOI:10.1038/nnano.2009.311>.

Menasco, W. et al., "Handbook of Knot Theory", Choice: Current Reviews for Academic Libraries, 2005, vol. 44, 502 pages <DOI:10.1016/B978-0-444-51452-3.X5000-X>.

Mirkin, C. et al., "A DNA-based method for rationally assembling nanoparticles into macroscopic materials", Letters to Nature, Aug. 1996, vol. 382, pp. 607-609 <DOI:10.1038/382607a0>.

Nedev, S. et al., "Optical Force Stamping Lithography", Nano Letters, Oct. 2011, vol. 11, No. 11, pp. 5066-5070 <DOI:10.1021/nl203214n>.

Nishiguchi, K. et al., "Room-temperature-operating data processing circuit based on single-electron transfer and detection with metal-oxide-semiconductor field-effect transistor technology", Applied Physics Letters, May 2006, vol. 88, article 183101, 4 pages <DOI:10.1063/1.2200475>.

Pal, S. et al., "DNA Directed Self-Assembly of Anisotropic Plasmonic Nanostructures", Journal of the American Chemical Society, Oct. 2011, vol. 133, No. 44, pp. 17606-17609 <DOI:10.1021/ja207898r>.

Pal, S. et al., "Quantum Efficiency Modification of Organic Fluorophores Using Gold Nanoparticles on DNA Origami Scaffolds", The Journal of Physical Chemistry, May 2013, vol. 117, No. 24, pp. 12735-12744 <DOI:10.1021/ip312422n>.

Park, S. et al., "Finite-Size, Fully Addressable DNA Tile Lattices Formed by Hierarchical Assembly Procedures", Angewandte Chemie, Jan. 2006, vol. 45, pp. 735-739 <DOI:10.1002/anie.200503797>.

* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
agggwtgatg ygtggtaggc                                                    20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
agggtagghg tggatgatgc                                                    20

<210> SEQ ID NO 3
<211> LENGTH: 20
<212> TYPE: DNA
<213> ORGANISM: Artificial Sequence

```
<220> FEATURE:
<223> OTHER INFORMATION: synthetic

<400> SEQUENCE: 3
taggttwtgg gtagggtggt                                                      20

<210> SEQ ID NO 4
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 4
ntaggdtggg tagggtggtn                                                      20
```

STRUCTURE ASSISTED DIRECTED EVOLUTION OF MULTIVALENT APTAMERS

CROSS-REFERENCE TO RELATED APPLICATIONS

This application claims the benefit of U.S. Application Ser. No. 62/372,680, filed Aug. 9, 2016, which is incorporated by reference herein as if set forth in its entirety.

STATEMENT REGARDING FEDERALLY SPONSORED RESEARCH

Not applicable.

FIELD OF THE INVENTION

The present invention relates to the fields of structural DNA nanotechnology, synthetic biology, molecular biology, and related fields.

BACKGROUND

The central task of nanotechnology is to organize and control matter with nanometer precision. To achieve this, scientists have studied the properties and behaviors of a large variety of materials including inorganic materials (e.g., carbon nanotubes and nanoparticles), organic molecules, and biological polymers (e.g., DNA, RNA, and proteins), as well as the methods to synthesize these materials using so-called "bottom-up" and "top-down" approaches. Among the field's significant achievements is the success of DNA self-assembly in building programmable nanopatterns; this breakthrough has attracted broad attention for its convenience and remarkable capacity to build novel, designer nanoarchitectures. DNA is an excellent nanoconstruction material for four reasons. First, the Watson-Crick base-pairing makes the hybridization between DNA strands highly predictable. Second, the structural features of B-form double helices are well-understood; the diameter and helical repeat have been determined to be ~2 nm and ~3.4 nm (i.e., ~10.5 bases), respectively, which facilitates modeling of even the most intricate DNA nanostructures. Third, modern organic chemistry and molecular biology techniques stock a diverse toolbox that can be accessed to readily synthesize, modify, and replicate DNA molecules. Finally, DNA is a biocompatible material, making it suitable for constructing multi-component nanostructures made from hetero-biomaterials.

A number of issues must be addressed before more advanced structures and applications can be developed using DNA origami technology. The most significant challenges are the high cost of DNA and the high error rate of self-assembly. Accordingly, there remains a need in the art for improved methods for achieving highly complex DNA nanostructures.

BRIEF SUMMARY

Provided herein are methods for the structure-assisted evolution of multivalent ligands, also known as multimeric aptamers, that have high affinity and specificity for a target molecule. In a first aspect, provided herein is a method for directed evolution of multivalent aptamers, the method comprising (a) linking a random library of nucleic acid sequences for aptamer selection to a defined single-stranded DNA (ssDNA) or RNA origami nanostructure, wherein the random library comprises two 20-mer random loop sequences; (b) immobilizing a benchmark target polypeptide on a bead; (c) contacting benchmark polypeptide-coated beads to the scaffold-linked library; (d) recovering the contacted beads; (e) eluting bound nucleic acid sequences from the contacted beads; (f) amplifying the eluted nucleic acid sequences using a forward primer and a reverse primer, wherein the reverse primer has an extended sequence to generate amplification products of different sizes; (g) separating the amplification products on a denaturing gel; and (h) recovering sense single-stranded DNA (ssDNA) for one or more subsequent rounds of directed evolution. The random library can have a total length of about 145 nucleotides. The nucleic acid origami nanostructure can be a Y-shaped ssDNA or ssRNA origami nanostructure. The bead can be a magnetic bead. The benchmark target polypeptide can be a polypeptide to which the multivalent aptamers will have binding affinity.

In another aspect, provided herein is a method for generating an amplifiable single-stranded DNA nanostructure, the method comprising applying a paranemic DNA crossover folding scheme to a ssDNA strand to form a paranemic, multidimensional ssDNA origami nanostructure, wherein the origami nanostructure comprises a single long DNA strand and can be replicated by DNA polymerases.

In a further aspect, provided herein is a method for directed evolution of multivalent aptamers, the method comprising (a) linking a random library of nucleic acid sequences for aptamer selection to a defined scaffold, wherein the scaffold comprises a nucleic acid origami nanostructure; (b) immobilizing a benchmark target polypeptide on a bead; (c) contacting benchmark polypeptide-coated beads to the scaffold-linked library; (d) recovering the contacted beads; (e) eluting bound nucleic acid sequences from the contacted beads; (f) amplifying the eluted nucleic acid sequences using a forward primer and a reverse primer, wherein the reverse primer has an extended sequence to generate amplification products of different sizes; (g) separating the amplification products on a denaturing gel; and (h) recovering sense single-stranded DNA (ssDNA) for one or more subsequent rounds of directed evolution. The defined scaffold can be a single-stranded DNA or RNA origami nanostructure. The ssDNA origami nanostructure can be a Y-shaped ssDNA origami nanostructure. The random library can have a total length of about 145 nucleotides. The bead can be a magnetic bead. The benchmark target polypeptide can be a polypeptide to which the multivalent aptamers will have binding affinity.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The present disclosure will be better understood and features, aspects, and advantages other than those set forth above will become apparent when consideration is given to the following detailed description thereof. Such detailed description makes reference to the following drawings, wherein.

Figures 1A, 1B:
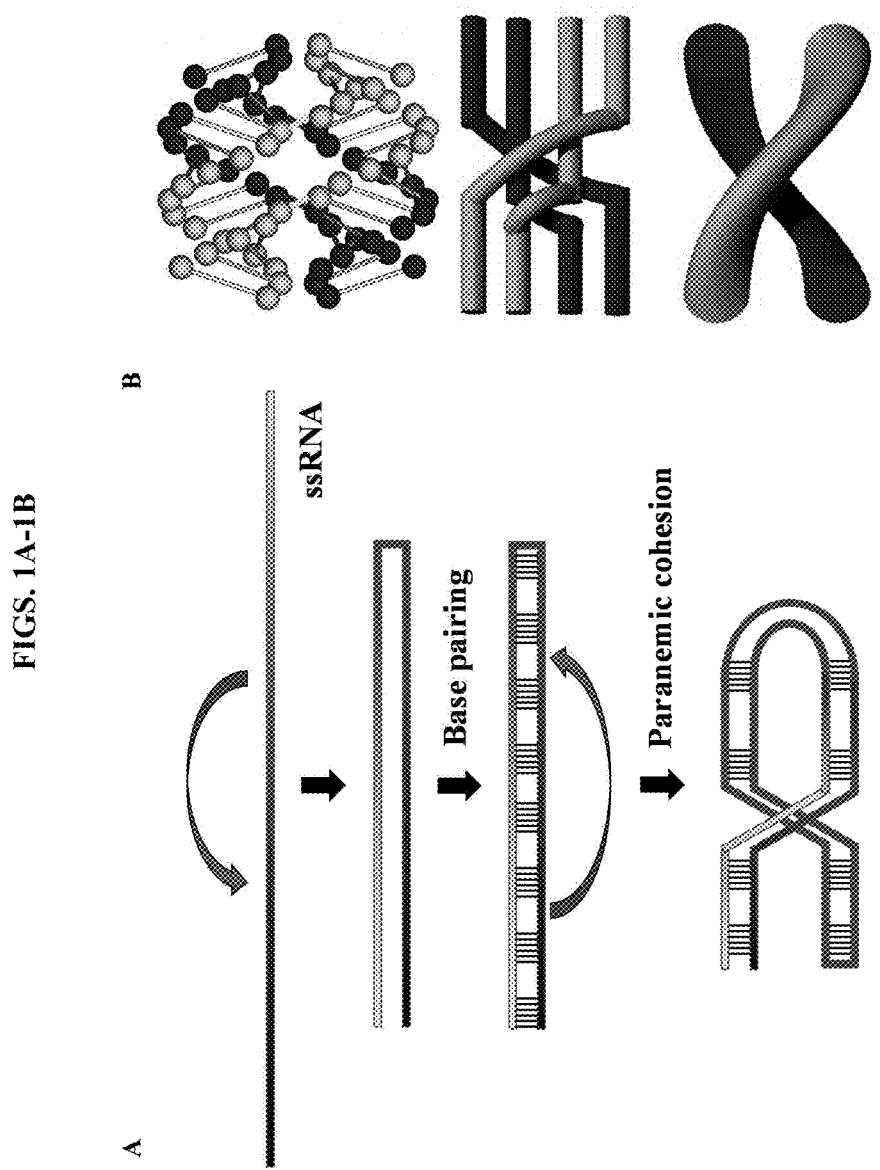
FIGS. 1A-1B illustrate ssDNA origami design and folding rules. (A) The two-step folding strategy. (B) X-shape paranemic cohesive interaction module.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

Nucleic acid origami structures, also referred to herein as DNA origami structures or DNA origami, are two- or three-dimensional arbitrary shapes formed from nucleic acids. The term "origami" infers that one or more strands or building blocks of DNA (called scaffold strands) may be folded or otherwise positioned into a desired structure or shape. Folded DNA origami are a simple and efficient way of creating two- and three-dimensional predetermined structures. Traditional scaffolded DNA origami structures are based on anti-parallel DNA crossover topology and multiple (typically hundreds) staple strands prevent DNA polymerase-mediated replication. For example, DNA origami technology has involved hybridization of short single-stranded DNA segments to a long single-stranded scaffold DNA strand, and the desired DNA origami structure is created by formation and stabilization of the scaffold.

The methods and systems provided herein are based at least in part on the inventors' development of a novel self-replicating system that enables the scalable production of designer nucleic acid origami nanostructures, with a focus on achieving low-cost, highly accurate sophisticated assemblies. The methods and systems provide for the evolution of high affinity and high specificity multivalent aptamers (e.g., high affinity and high specificity synthetic antibodies) against any protein targets. Evolved multivalent aptamers obtained according to the methods provided herein can be used in a variety of applications including, for example, diagnostics, therapeutics, biosensing, and drug delivery. In particular, benefits of multivalency include the development of aptamer therapeutics for diseases that require simultaneous binding of two or more targets.

Accordingly, in a first aspect, provided herein is a method of using single stranded DNA or RNA nanostructures as structural supports to achieve structure assisted evolution of multivalent binding ligands. As used herein, the term "multivalent aptamer" refers to a construct comprising two or more identical or different nucleic acid aptameric binding motifs, meaning RNA or DNA molecules capable of tight and specific binding to their targets due to the formation of characteristic spatial structures. In some cases, multivalent aptamers comprise additional structural elements or functional groups. As described herein, the methods and systems of this disclosure advantageously direct the evolution of aptamers for high affinity and specificity toward their molecular targets.

In some cases, a method of structure-assisted evolution of multivalent aptamers comprises (a) linking a random library of nucleic acid sequences for aptamer selection to a defined scaffold, wherein the scaffold comprises a nucleic acid origami nanostructure; (b) immobilizing a benchmark target polypeptide on a bead; (c) contacting benchmark polypeptide-coated beads to the scaffold-linked nucleic acid library under conditions that favor binding of the benchmark polypeptide to nucleic acid sequences having affinity to the benchmark polypeptide; (d) recovering the contacted beads; (e) eluting bound nucleic acid sequences from the contacted beads; (f) amplifying the eluted nucleic acid sequences using a forward primer and a reverse primer, wherein the reverse primer has an extended sequence to generate amplification products of different sizes; (g) separating the amplification products; (h) repeating step (a) to step (g) for subsequent rounds of directed evolution as desired; and (h) recovering sense single-stranded nucleic acids (ssDNA or ssRNA) for the one or more rounds of directed evolution.

Molecular targets for the methods described herein can be any biological molecule against which a nucleic acid can bind with affinity and specificity. In certain embodiments, the molecular target is a polypeptide. Preferably, polypeptide molecular targets are polypeptides useful for or associated with detection, treatment, or prognosis of a disease or condition. For example, molecular targets include, without limitation, polypeptides expressed by a bacterium, virus, or other pathogenic microorganisms. The term "pathogenic" as used herein means harmful to human or animal health. For example, the pathogenic microorganism, e.g. pathogenic bacteria, may be one which causes food poisoning in humans. Methods for using aptamers, for example, for detection of molecular targets indicative of an infection are known and available in the art.

In certain embodiments, the nucleic acid origami nanostructure is a single-stranded DNA (ssDNA) or a single-stranded RNA (ssRNA) origami nanostructure. As used herein, the term "nanostructure" encompasses any structure having a distinct shape or form (including, without limitation, linear forms, circular forms, two-dimensional patterns, and three-dimensional structures) where at least one dimension of the structure is on the nanoscale, i.e., in the range between 0.1 and 100 nm. For example, a DNA origami nanostructure as described herein can may have at least one nanoscale dimension and comprise one or more single stranded nucleic acids. In some cases, single stranded nucleic acids hybridize to form at least a partially double-stranded structure having defined features and complex geometry. As used herein, the term "complex geometry" refers to a multi-dimensional arrangement or topology of molecules or chains of molecules comprising a structure.

Figures 10A, 10B:
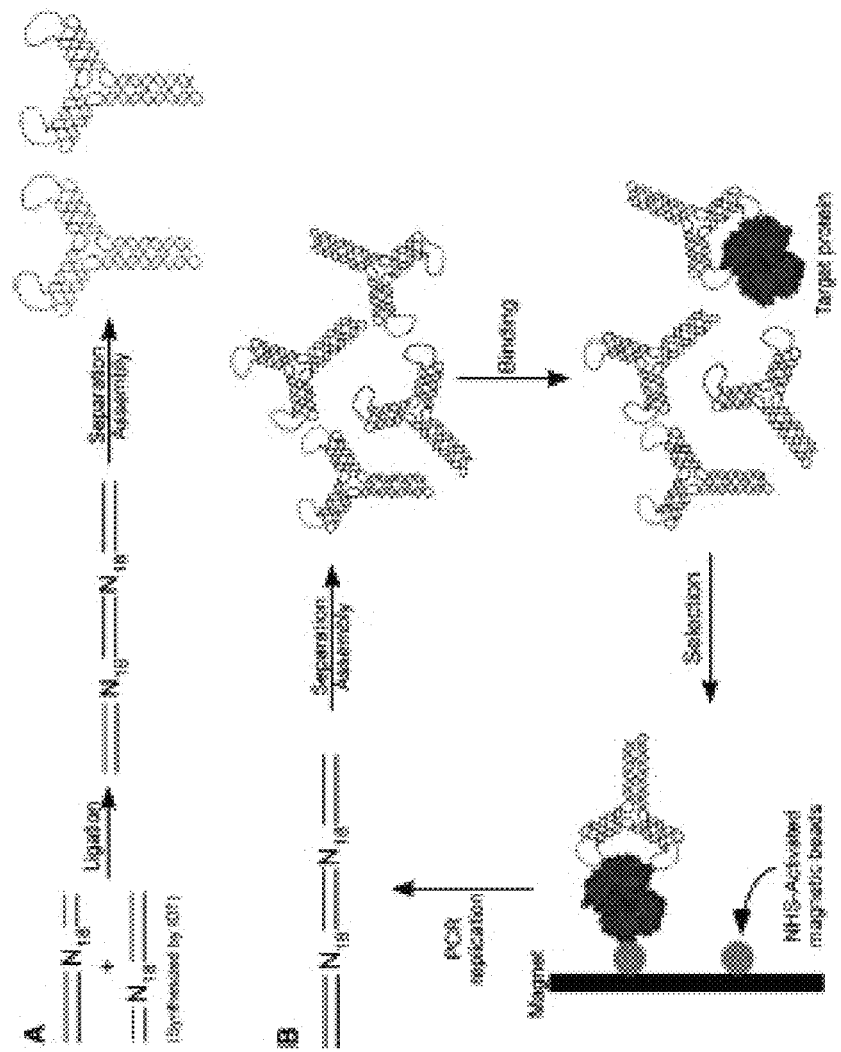
FIGS. 10A-10B illustrate exemplary methods of synthetic antibody library construction (A) and selection cycle (B).

A variety of suitable nucleic acid nanostructures are known in the art. Preferably, the nucleic acid nanostructure comprises a DNA origami. In some embodiments, the nucleic acid nanostructure comprises a spiral DNA scaffold or a DNA tile or tiling array. In preferred embodiments, nucleic acid nanostructure are formed by folding as described herein. In other cases, nucleic acid nanostructures can be formed by base pairing of single stranded DNA or derivatives thereof or by other non-covalent linkage, such as biotin-streptavidin interaction. Referring to FIGS. 10A-10B, the nucleic acid origami nanostructure can be a Y-shaped DNA origami nanostructure. In some cases, the nucleic acid origami nanostructure is a Y-shaped nanostructure comprising single-stranded DNA.

In some cases, the ssDNA or ssRNA origami nanostructure is obtained by applying a paranemic DNA crossover folding scheme combined with n-arm DNA junction vertices to a single stranded nucleic acid to form a paranemic single stranded nucleic acid origami nanostructure. As used herein, the term "paranemic" refers to a DNA structure in which the participating strands can be separated without mutual rotation of the opposite strands. Accordingly, the term "paranemic crossover" or "paranemic motif" as used herein refers to a motif for assembling two nucleic acid molecules using Watson-Crick (WC) base-pairing without unfolding preformed secondary structure in the individual molecules. Advantageously, paranemic crossover motifs include reversible binding without strand entanglement or disruption of internal helices. Paranemic motifs generally contain a central dyad axis that relates two flanking parallel double helices that are interwrapped to form a four-stranded, coaxial nucleic acid structure in which the strands are held together by Watson-Crick base pairing. As used herein DNA is deoxyribonucleic acid obtained from any source, natural or recombinant, and includes without limitation, single stranded DNA, double stranded DNA, cDNA, and any other known or subsequently prepared or discovered DNA. RNA is ribonucleic acid obtained from any source, natural or recombinant, and includes, but is not limited to RNA, mRNA, cRNA, tRNA, nRNA, rRNA and any other known or subsequently prepared or discovered RNA.

In some cases, the nucleic acid origami nanostructure is a single-stranded DNA (ssDNA) capable of being replicated in vitro and in vivo using various amplification methods. In some cases, the ssDNA origami nanostructure can be replicated by DNA polymerases. Advantageously, such methods of obtaining ssDNA or ssRNA origami nanostructures enable scaling up of defined DNA origami nanostructures for a variety of practical applications.

Assembled ssDNA origami nanostructures can be characterized using various techniques. For example, ssDNA origami structures can be characterized using microscopic techniques, such as transmission electron microscopy (TEM), atomic force microscopy (AFM), and gel electrophoresis assays. TEM is especially useful for the structural characterization of 3D origami structures and AFM is particularly useful for the analysis of 2D structures. An important feature of our ssDNA origami is the knotted conformation with high crossing numbers. Characterization methods such as gel electrophoresis can assess topology via markers similar to those used to investigate topological DNA structures such as the Borromean rings.

Figure 6:
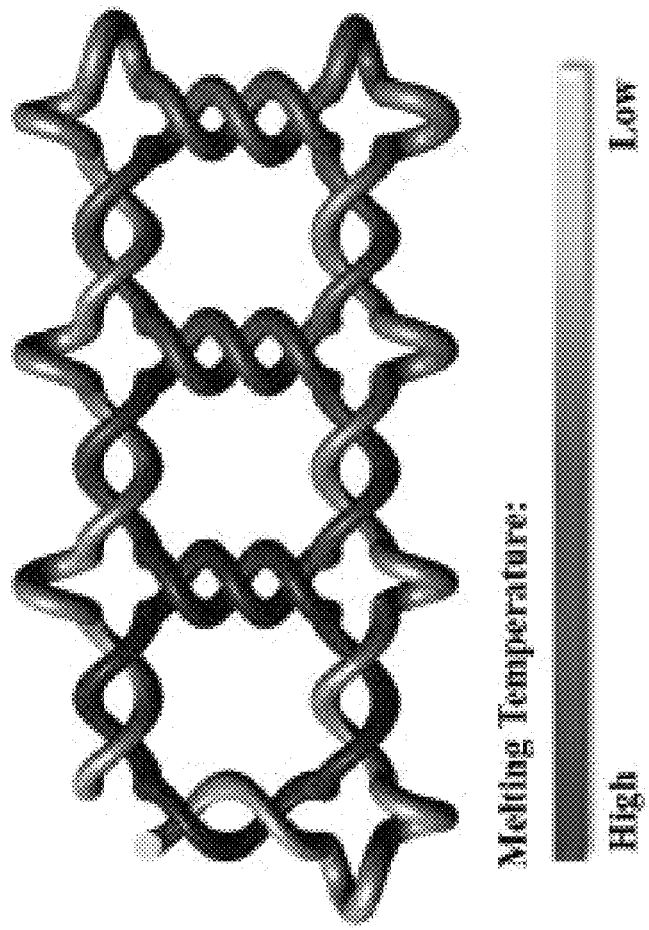
FIG. 6 illustrates hierarchical folding order in an exemplary nanostructure. The scale indicates the forming/melting temperature.

In some cases, it can be advantageous to design and construct a series of knots and 3D ssDNA origami nanostructures. Referring to FIG. 6, hierarchical folding can avoid unwanted topological traps. The structure is assigned heterogeneous sequences in paranemic interaction regions having different GC content, which will in large part determine the regions' annealing/melting temperature. By carefully designing the knotting order, areas that should form first and last will be assigned the highest GC contents, respectively. For experimental optimization, the methods provided herein can comprise assessing appropriate annealing programs to form desired ssDNA origami nanostructures. Parameters that can be optimized include the annealing temperature ramp and cation concentration in a sample solution (varied to achieve improvements in target structure folding).

In some cases, the ssDNA origami sequence used for structure assisted evolution can be cloned into plasmids and replicated in bacteria such as *E. coli*. See FIG. 9A. Because long, inverted repeat sequences of long ssDNAs can be susceptible to DNA rearrangements due to recombination events within those repeated regions, it can be advantageous to use bacterial strains that tolerate long, direct, and inverted repeat sequences and reduces recombination of cloned DNA. For example, unique *E. coli* strain such as NEB stable *E. coli* (New England Biolabs) can be used. As described in the Examples section, we successfully cloned a 6.6-kb DNA sequence containing a hairpin structure into NEB stable *E. coli* strain and replicated the plasmid in vivo without recombination. After plasmid DNA isolation, ssDNAs were generated through restriction and nicking endonuclease treatment and denaturing gel separation. In this example, nicking endonuclease cutting sites (Nb.BbvCI and Nt.BbvCI) were originally engineered inside the DNA sequences. The unique feature of Nb.BbvCI and Nt.BbvCI is that they cleave sense and antisense strand of the same dsDNA substrate, respectively, because they are the two domains of the restriction endonuclease BbvCI. By separately using these two nicking endonucleases, both sense and antisense ssDNA are obtained. One advantageous feature of our design is that both the sense and antisense strands will fold into the same geometrical structures, each as a complimentary copy to the other.

Figures 9A, 9B, 9C:
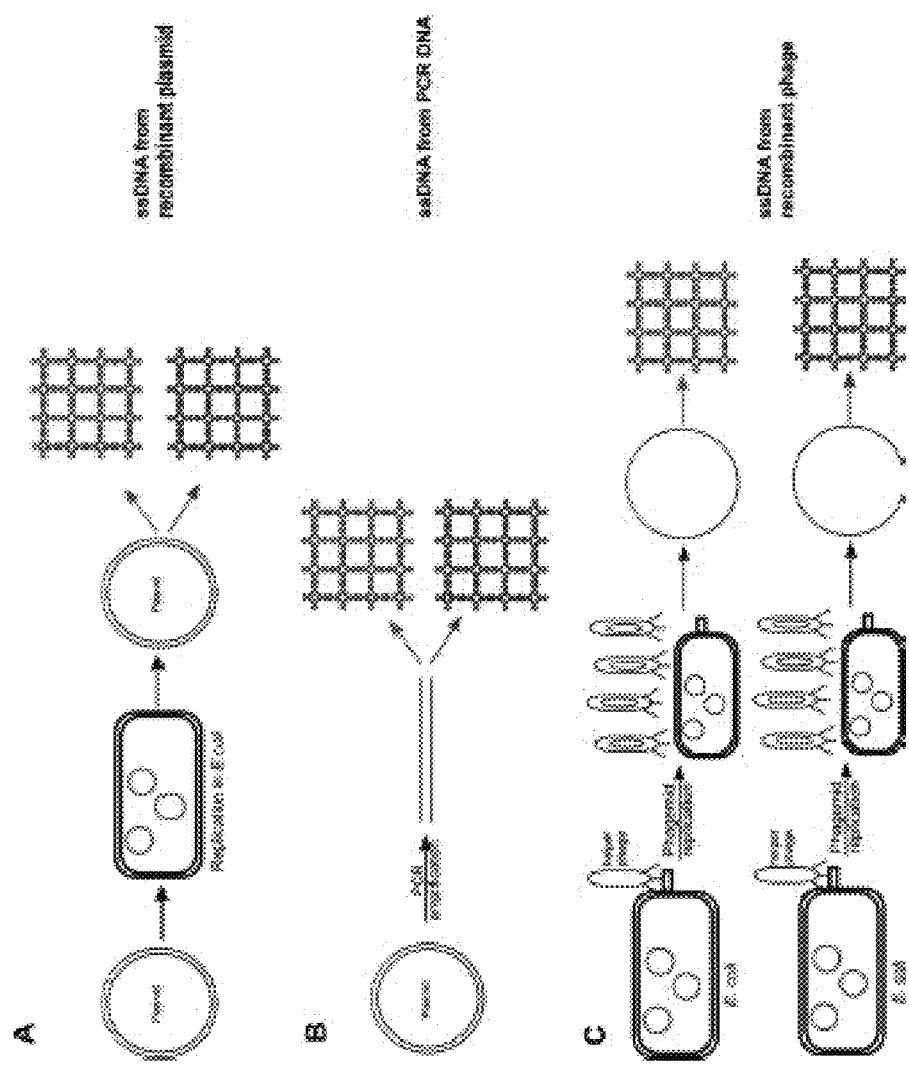
FIGS. 9A-9C illustrate three exemplary replication methods for ssDNA origami. (A) Replication of DNA sequences in a plasmid, (B) PCR amplification, and (C) ssDNA replication using an M13 phage system.

In some cases, PCR can be used to replicate ssDNA origami sequences (FIG. 9B). Since its discovery in 1983, PCR has been a common and indispensable technique for in vitro gene replication in all biological laboratories. One challenge is that ssDNA origami sequences can contain several kilobases of inverted repeat sequences, which may inhibit efficient and specific amplification by normal DNA polymerases. Accordingly, it can be advantageous to use an engineered PCR enzyme, Q5 High-Fidelity DNA polymerase (New England Biolabs). With the lowest error rate and highest amplification processivity of all commercially available DNA polymerases, Q5 High-Fidelity DNA polymerase is ideal for long and difficult amplicons. Other DNA polymerases, such as Phusion DNA polymerase and Phire Hot Start II DNA polymerase, could also be used for the amplification, although these polymerases may be associated with higher error rates. Other PCR additives (e.g., betaine and dimethyl sulfoxide) that decrease amplicon secondary structures can also be employed to improve PCR efficiency. After DNA been amplified, ssDNAs can be obtained and folded using the same technique described in the first replication method.

A third replication method that can be employed uses utilizing M13 bacteriophage vectors for in vivo replication. Referring to FIG. 9C, the M13 bacteriophage contains a circular ssDNA genome, providing a perfect system for ssDNA amplification as no dsDNA separation is required. Although the wild-type M13 phage genome is only 6.4 kb, it has been reported to pack DNA up to 7 times longer into its phage particles. Therefore, it is feasible to replicate large ssDNA origami sequences using the M13 phage. After being cloned into a phagemid vector, ssDNA origami sequences can replicate as plasmid DNA in *E. coli* until helper phages are introduced for the infection. Upon infection, M13 helper phage expresses all of the M13 proteins required for phagemid vector ssDNA replication and virus assembly. Because of the defective replication and packaging signal within the helper phage genome, most of the phage particles contain phagemid ssDNA. ssDNAs are easily purified from the harvested M13 phage particles. After isolating the M13 ssDNA, the origami structures can be directly self-assembled without additional enzymatic treatment. Thus, the cost of ssDNA origami will be theoretically equivalent to that of obtaining the traditional DNA origami scaffold.

Of these replication methods, the first and third methods are preferred because they only involve DNA replication in *E. coli* cells. Because *E. coli* cells already possess various machinery for the DNA replication process, including DNA repair systems, DNA replication is very efficient and accurate. The mutation rate of the *E. coli* replication system has proven to be only approximately $10^{-10}$, which is four orders of magnitude lower than the highest fidelity PCR polymerase, Q5 High-Fidelity DNA polymerase. Replication in *E. coli* cells can also be easily scaled up by growing large volume fermentation cultures to further reduce the cost compared with PCR replication.

In some cases, the random loop sequences have a length of about 10, 11, 12, 13, 14, 15, 16, 17, 18, 19, 20, 25, 30, or 40 nucleotides (inclusive). The random library can have a total length of about 120 nucleotides to about 185 nucleotides. In certain embodiments, the random library has a length of about 145 nucleotides. The nucleic acid origami nanostructure can be a single-stranded DNA origami nanostructure. The nucleic acid origami nanostructure can be a Y-shaped DNA origami nanostructure. The bead can be a magnetic bead. The benchmark target polypeptide can be a polypeptide to which the multivalent aptamers will have binding affinity.

Referring to FIGS. 10A-10B, a library of sequences is created using two random sequences embedded into a Y-shaped DNA origami nanostructure that can mimic an antibody. Gene fragment libraries comprising consecutive random nucleotides can be readily synthesized using methods known in the art. In some cases, the random library of nucleic acids comprises two 20-mer random loop sequences. The two sets of gene fragment libraries can be joined together to complete a Y-shaped nanostructure. Upon separation, the sense and antisense strands will self-assemble into two sets of libraries that are completely replicable in vitro. Systematic evolution of ligands by exponential enrichment (SELEX) is powerful technique that is commonly used for in vitro selection. For the methods provided herein, selection cycles are performed using constructed libraries against target molecules such as proteins. In some cases, Y-shaped nanostructures without random sequences and only one set of random sequences can be included as competitors for more stringent selection. With short, random sequences embedded in the long, fixed DNA sequences, PCR amplification bias will be minimal. After several rounds of selection, the enriched population of ssDNA nanostructures can be sequenced using, in preferred embodiments, a high-throughput next-generation sequencing technique. One sequencing reaction generates millions of reads that provide abundant information for the dual aptamer regions. Binding affinity and specificity can be evaluated using the determined sequences.

In some cases, multivalent aptamers obtained according to the methods provided herein can be used as biological recognition elements of biosensors. Aptamer-based biosensors often use immobilized aptamers as recognition elements for the target molecules. The most popularly used electrode material is gold where the thiolated DNA/RNA strands, in this case aptamers, can be immobilized via strong Au—S linkage. In other cases, a streptavidin-biotin linkage is used to immobilize aptamers. In some cases, fluorescent or other detectable moieties are linked to an aptamer. The term "biosensor" as used herein may be any biosensor which comprises the aptamers obtained according to a method described herein. It will be understood that antibodies used as biological elements may be replaced with aptamers in biosensor applications. This change enables a rapid method to detect, for example, pathogenic microorganisms. The advantages of using aptamers over antibodies include the lower costs of production, stability at room temperature, and there are no ethical issues when aptamers are used because they can be produced by a chemical synthesis where no animals or animal cells are needed. Another advantage of aptamers is that they can be stored as a lyophilized powder at room temperature for more than one year. In addition aptamers can recover their native active conformation after denaturation.

In some cases, multivalent aptamer sequences obtained according to the methods described herein may be refined (e.g. by random or directed mutagenesis) to alter the base sequence in order to generate aptamer molecules with greater target affinity or specificity.

Figures 2A, 2B, 2C:
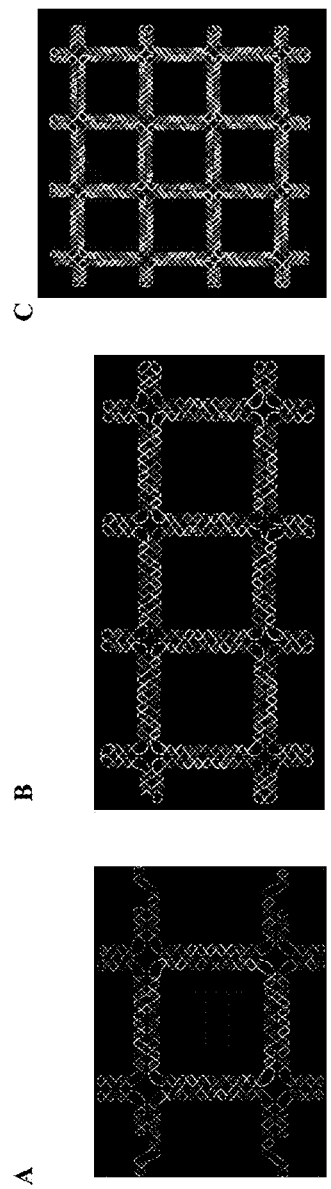
FIGS. 2A-2C illustrate ssDNA origami with crossing numbers. (A) 1.7 k square structure with 9 crossing numbers. (B) 3.6 k 3-square structure with 23 crossing numbers. (C) 7.5 k 9-square structure with 57 crossing numbers.

The basic building blocks for the unique paranemic DNA origami folding methods described herein illustrated in FIGS. 1A-1C. Two parallel double helices (blue and grey) interwind into right-handed chirality. In certain embodiments, the single-stranded nucleic acid is single stranded DNA (ssDNA) or RNA (ssRNA) or derivatives thereof. As described herein, complex ssDNA origami nanostructures are formed by routing ssDNA into various shapes to form paranemic crossover topology. The simple square structure shown in FIGS. 2A-2C illustrates the relationship between designer DNA nanostructures and the topological interpretation of helices. The target shape comprises 4 four-arm motifs at each corner. The geometric requirements of four-arm motifs are satisfied by designing $T_4$ loops in the center of the junctions to maintain the 90 degree angle. Each edge of the square is a connection for two or three of the paranemic crossover building blocks illustrated in FIG. 2. By assigning appropriate crossing numbers on each edge and bridging the building blocks at each junction (corner of the square), the whole structure is formed from ssDNA. Referring to FIG. 2A, the square design has a crossing number of 9, which topologically equals knot 91 in the table of knots. The simple square structure already has a crossing number of 9, which is not small according to knot theory. As of 2005, researchers had only tabulated prime knots up to 16 crossings. Design of more complex structures, which require large crossing numbers, which will dramatically increase the topological complexity of our ssDNA nanostructures.

There are several crucial considerations to ensure successful folding of ssDNA origami. First, wireframe origami design has very different folding paths than traditional compact origami routing. Enough cavities are left in the pattern to provide space to allow DNA strands to wind through each other while forming the target structure. Second, although the structure has large total crossing numbers, they are evenly distributed in the structure. Every edge has a small number of crossing points (2 to 3 are represented here). Third, the length of each edge can be neither too long (which requires more crossing points to stabilize the formation) nor too short (which leads to smaller cavities inside patterns). A balance between cavity size and the crossing number on each edge can be tested and modified. Finally, other important parameters (e.g., numbers of arms stretching from the vertices and numbers of crossovers in each arm) can be evaluated to optimize design. Appropriate crossovers are assigned in certain locations to enable ssDNA to weave through the entire structure while minimizing any unfavorable bending due to stress.

Cloning and Replicating ssDNA Origami Nanostructures

Any suitable methods can be used to replicate ssDNA origami sequences. In some cases, cloning ssDNA comprises synthesizing double-stranded (ds) DNA containing the sequences of the ssDNA nanostructure (sense strand) and its fully complementary strand (antisense strand). In order for this dsDNA to be accurately replicated in *E. coli*, it is cloned into a plasmid. In some cases, the first step of cloning ssDNA origami nanostructure genes is to assign and synthesize the DNA sequences. Using a design software program such as Tiamat software[78] to design the ssDNA origami nanostructures, the DNA sequences can be generated in silico, preferably with minimized direct DNA repeats, limited G repetitions, and optimized overall GC content (approximately 50%). The ideal percentage range of GC content in all regions of the DNA sequences is between 30% and 70%. Peaks outside of this range can adversely affect both DNA synthesis and replication. Accordingly, it is recommended to inspect the DNA sequence for GC content. The DNA sequences can be further analyzed and modified to assign unique restriction enzyme sites for cloning purposes.

Another significant challenge of ssDNA origami gene cloning is the complex secondary structure. If designed according to the ssDNA origami design rules presented herein, the ssDNA will first assemble into a large hairpin structure with several mismatches allowed for paranemic cohesion. This structure causes a large DNA inverted repeat sequences that prevent DNA artificial synthesis. However, this problem can be avoided by dividing the full-length DNA sequence into two segments and individually synthesizing and cloning them. With optimized DNA sequences, neither segment will contain strong secondary structures and, thus, are easier to synthesize and clone into plasmid vectors. After the two DNA segments are completely synthesized and cloned into the plasmid vector, DNA sequencing can be carried out to ensure accuracy. If mutations are identified, site-directed mutagenesis can be performed to correct the mutations. After we obtain the correct clones, subcloning is performed to combine the two segments into a single vector using the designed restriction enzyme sites. Because no PCR is performed during the subcloning step, further DNA sequencing is not necessary.

Scaling Up ssDNA Origami Sequence Size or Structure

An objective of DNA structural nanotechnology is to scale up the available surface or size of DNA origami nanostructures because the number of unique addresses at which nanometer-scale materials can be organized will increase proportionally. DNA nanostructure arrays are normally formed by connecting the same or different DNA tiles/origami structures through sticky end cohesion. This is not applicable to ssDNA origami as it does not contain single-strand sticky ends. Instead, ssDNA nanostructures can be formed by ssDNA origami through paranemic crossover (PX) cohesions. The half PX tile is designed to protrude outside of the structure, allowing it to serve a role similar to that of sticky ends. Another structure (e.g., its complementary sequence) containing another half PX can be hybridized via PX cohesion. Accordingly, 1-dimensional (1D) and multi-dimensional (e.g., two dimensional or 2D) ssDNA origami arrays can be prepared.

In some cases, ssDNA origami can be scaled up by increasing ssDNA size to form a larger ssDNA origami nanostructure. With the development of synthetic biology, especially the invention of large synthetic DNA assembly technology (e.g., Gibson assembly), it is now feasible to synthesize DNA molecules up to several hundred kilobases. Although the in vitro synthesis of long DNA is not a major issue, we predict that the replication of large amounts of long ssDNA will be the limiting factor that affects the size of ssDNA we could obtain. To replicate long DNAs in *E. coli* cells, they will be cloned into cloning vectors. Traditional cloning vectors including plasmid vectors, bacteriophage vectors, and cosmids have size limits up to 50 kb for DNA insert. Although bacterial artificial chromosomes (BACs) can insert up to 350 kb of exogenous DNA, they are maintained in *E. coli* cells with a copy number of only 1 per cell. Therefore, the BAC cloning system is not a perfect method for producing large quantities of ssDNA. PCR was reported to be able to amplify DNAs up to 30 kb, but it is also not very efficient for obtaining large quantities in the case of 30 kb DNA. Moreover, mutation is another concern related to long DNA amplification. In conclusion, current technology would enable scaling up the high-quantity replication of ssDNA origami nanostructures up to 50-kb.

Functional ssDNA Origami Nanostructures

Since the ssDNA origami described herein is self-assembled from a single long ssDNA, DNA overhang hybridization is not an option for co-assembly with other molecules. However, it is possible for ssDNA origami nanostructures to serve as fully addressable molecular pegboards using DNA motifs that can be designed into the ssDNA sequences. Such DNA motifs include, without limitation, DNA aptamers, DNA stem-loops, and half PX tiles. As used herein, the term "aptamer" refers to oligonucleotide molecules having secondary structures that allow binding to specific target molecules (e.g., proteins, sugars, drugs, etc.). We previously reported aptamer-directed self-assembly of proteins on DNA nanostructures. The aptamer comprises nucleic acid sequence that does not participate in base-pairing with other polynucleotides within the nucleic acid nanostructure.

DNA aptamers can be introduced into ssDNA origami by incorporating the aptamer sequence during DNA synthesis. In this manner, the ssDNA origami is specifically associated with an aptamer target without disrupting ssDNA origami topology. Aptamers can be synthesized and screened by any suitable methods in the art. For example, aptamers can be screened and identified from a random aptamer library by SELEX (systematic evolution of ligands by exponential enrichment). In certain embodiments, aptamers that bind to a cell surface target molecule can be suitably screened and selected by a modified selection method herein referred to as cell-SELEX or cellular-SELEX, even if the identity of the cell surface target molecule is unknown. As used herein, the term "binding to" or "bound to" refers to any of direct binding, indirect binding, covalent binding, or non-covalent binding, unless otherwise specifically indicated.

The other two DNA motifs, DNA stem-loop and half PX tile, rely on specific DNA oligonucleotide hybridization. A DNA stem-loop structure contains a long single-stranded loop region (25-30 nucleotides) that allows the hybridization of a complementary oligonucleotide that can be modified at either the 5'- or 3'-end to incorporate other molecules (e.g., proteins), which will thus be organized on the ssDNA origami. Distinct sequences can be introduced to the loop region, allowing the organization of multiple components on the same ssDNA origami nanostructure. The half PX motif is the half paranemic cohesion unit that can pair with the other half unit to form the complete PX structure. When a half PX motif is incorporated into the ssDNA origami, other molecules connected with the other half are specifically organized on the ssDNA origami. The thermodynamic stabilities and rigidities of interaction motifs will be further analyzed. One of the key features of the ssDNA origami methods provided herein is the relatively low cost due to its replicability.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Directed Evolution of Functional DNA Nanostructures

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

Unless otherwise indicated, any nucleic acid sequences are written left to right in 5' to 3' orientation; amino acid sequences are written left to right in amino to carboxy orientation, respectively.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Examples.

EXAMPLES

This example demonstrates the design, construction, and replication of ssDNA origami nanostructures.

We designed and constructed a square DNA structure formed from a 6.6-kb DNA based on the paranemic DNA crossover topology. The square lattice wireframe ssDNA had a crossing number of 57. The two terminal ends needed to wind through the whole frame 57 times in the correct order. The high-resolution atomic force microscope (AFM) images shown in FIGS. 5A-5C confirm that the formed structures have tight, neat edges. We also observed partially formed structures with blurred edges and DNA loop coils. To further verify the winding process, we used the AFM tip and attempted to scratch the structures. The DNA strands on partially formed structures could be easily scratched out, while the well-formed structures maintained their integrity.

Figures 5A, 5B, 5C:
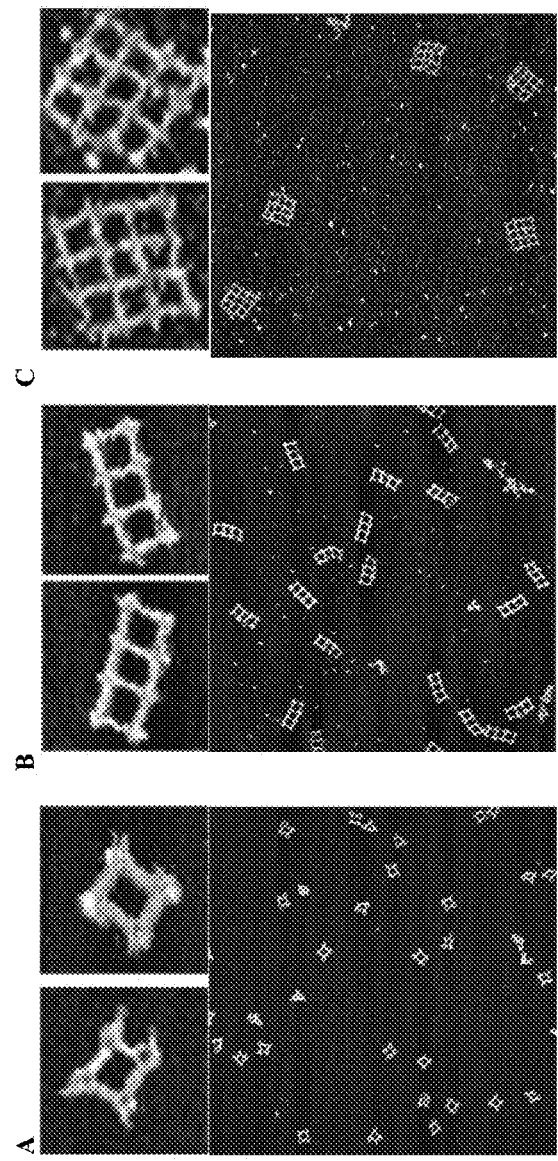
FIGS. 5A-5C present AFM (atomic force microscopy) images for ssDNA origami with 9 crossing numbers (A), 23 crossing numbers (B), and with 57 crossing numbers (C). The zoom-in images are 100 nm×100 nm scale and the zoom-images are 1 um×1 um scale.

To test the M13 phage replication strategy, the square DNA structure formed from a 6.6-kb DNA was artificially synthesized and cloned into a pUC57 plasmid. The sequence was completely replicable in vivo using an *E. coli* DNA polymerase and was also easily amplified by PCR in vitro. Upon nicking endonuclease treatment, ssDNAs from either sense or antisense strands were purified and refolded into the correct structures (FIGS. 5A-5C). The successful assembly of this ssDNA origami nanostructure demonstrates that it is feasible to replicate 2D and 3D ssDNA nanostructures using the proposed methodology.

Design and Replicate Single-Stranded DNA Origami Nanostructures with High Crossing Numbers.

We successfully designed and replicated single stranded DNA origami nanostructures with high crossing numbers (crossing number reaching up to 57). The single stranded DNA fold following the structure formation of a paranemic crossover motif of different spacing. The single stranded DNA can be obtained by restriction enzyme digestion of the cloned product of synthetic genes bearing the designed sequences to form the paranemic crossover structures. We have successfully demonstrated that such single stranded DNA nanostructures can be obtained by both in vitro and in vivo amplification of the synthetic genes followed by the restriction digestion and thermal annealing.

To create a scalable ssDNA structure, we proposed a two-step folding strategy by using a simple DNA motif as modular building block (FIG. 1A). We developed a design strategy to route a long ssDNA into geometric shapes in two steps. First, half-length of one ssDNA will fold back to partially pair with the other half, leaving several unpaired single stranded regions. Secondly, those designed free regions will match each other by paranemic cohesive interactions and finally fold the target architecture. An individual DNA motif possesses two anti-parallel double helixes, representing half modular building block, as well as one pixel of any shapes in our design canvas. This DNA motif can be treated as an X-shape structure with right handed chirality along the double helices axis (FIG. 1B). Planning this X-shape paranemic crossover topology can produce complex ssDNA origami nanostructures. After selecting a target wireframe shape, we assigned appropriate crossing numbers on each edge and bridged the building blocks at each vertex. FIG. 2 shows various design with increasing crossing number from 9 to 57.

There are several crucial considerations to ensure the successful formation of our designs. First, enough cavities are left in the pattern to provide space to allow DNA strands to wind through each other while forming the target structure. Second, although the structure has large total crossing numbers, they are evenly distributed in the structure. Every edge has a small number of crossing points (2 to 3 are chosen here). Third, the length of each edge can be neither too long (which requires more crossing points to stabilize the formation) nor too short (which leads to smaller cavities inside patterns). A balance between cavity size and the crossing number on each edge needs to be tested and optimized. Finally, other important parameters (e.g., numbers of arms stretching from the vertices and numbers of crossovers in each arm) will be evaluated to optimize design. Appropriate crossovers will be assigned in certain locations to enable ssDNA to weave through the entire structure.

Figures 3A, 3B:
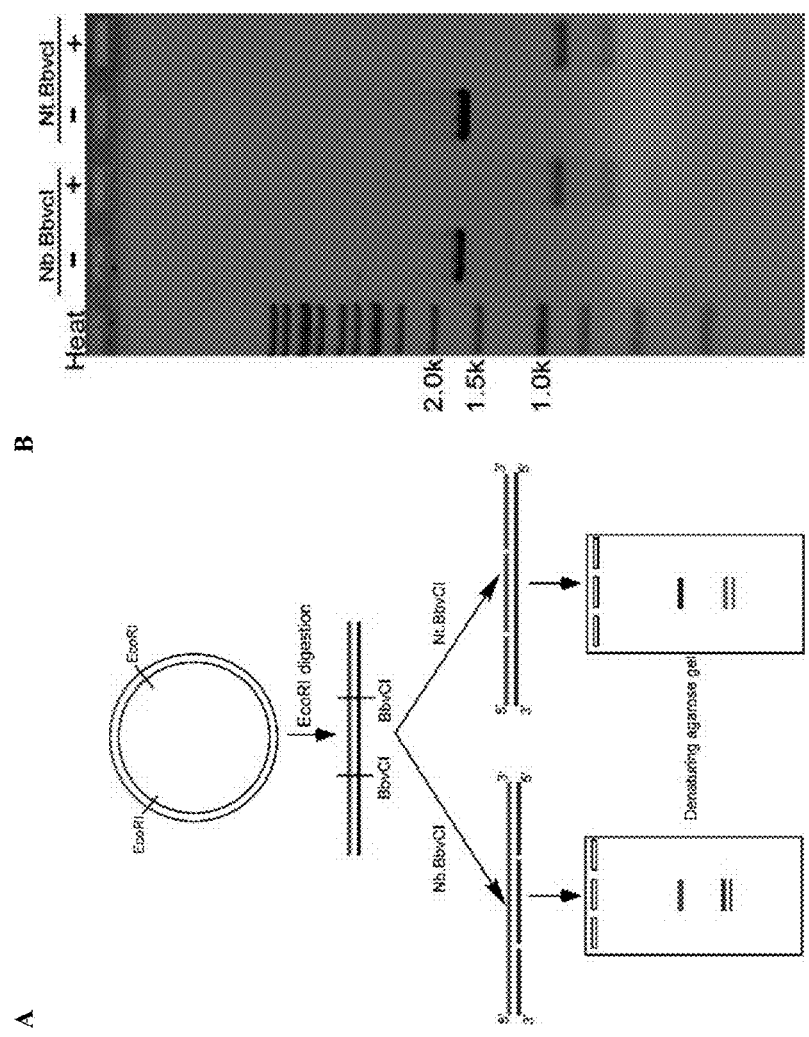
FIGS. 3A-3B demonstrate in vitro amplification of ssDNA. (A) Schematic of ssDNA generation by restriction enzyme and nicking endonuclease treatment of plasmid DNA. (B) Denaturing agarose gel electrophoresis of nicking endonucleases treated DNA. With heat denaturation, dsDNA was separated into several bands after Nb.BbvCI or Nt.BbvCI digestion. The largest band is the correct DNA and is gel purified.

These single-stranded DNA nanostructures can be obtained by both in vitro and in vivo amplification of the synthetic genes followed by the restriction digestion and thermal annealing. FIG. 3A shows the method for generating the single-stranded DNA molecules for a 1.7 k square structure. During the sequences design step, two nicking endonuclease Nb.BbvCI recognition sequences was embedded in our DNA sequence. After the plasmids containing ssOrigami genes were thus amplified in vivo as the bacteria population grows, the plasmids were purified and treated by the restriction enzyme EcoRI as well as the nicking endonuclease Nb.BbvCI or Nt.BbvCI. As a result, the plasmid DNA was separated in the denaturing agarose gel and the correct single-stranded DNA band was gel purified (FIG. 3B).

Figures 4A, 4B:
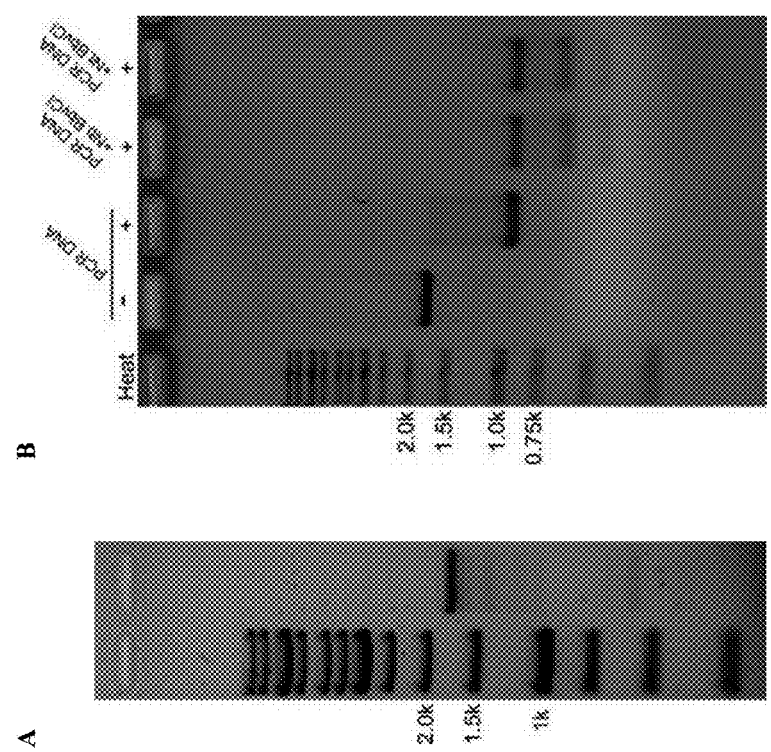
FIGS. 4A-4B illustrate PCR amplification of a 1.7 k ssDNA origami sequence. (A) PCR product of the 1.7 k ssDNA origami. (B) Optimized PCR reaction product with the addition of DMSO. Nicking endonuclease digestion was performed and ssDNAs were separated on a denaturing agarose gel.

An alternative method for amplification of the single-stranded DNA is through PCR method. The ssDNA origami gene contains a large portion of self-complimentary region, thus the PCR efficiency needs to be optimized. The PCR reaction using the high-fidelity Q5 DNA polymerase generated a strong band with several lower bands (FIG. 4A). Gel purification of the correct DNA band is thus required before the enzyme treatment to generate the ssDNA. In order to simplify this step and increase the yield, PCR reaction was optimized. DMSO was added to the PCR reaction mixture to a final concentration 5%. A strong single band was obtained with the addition of DMSO. The PCR product was then directly treated with nicking endonucleases without further purification and ssDNA was separated by denaturing agarose gel electrophoresis and gel purified.

Single-stranded DNA obtained from both in vitro and in vivo method was then self-assembled by a thermal annealing program. Atomic force microscope (AFM) was then employed to visualize the correct formation of ssDNA origami nanostructures with high crossing numbers (FIGS. 5A-5C).

Design and Replicate Single-Stranded DNA Origami with Zero Crossing Number.

In collaboration with Peng Yin's lab at Harvard University, we successfully designed and replicated a series ssDNA origami with zero crossing number. This was inspired by the fact that all the existing RNA secondary structures has zero crossing numbers to facilitate the folding of the tertiary structures. A design strategy that can produce zero crossing number ssDNA origami will simplify folding process and increase assembly yield. Therefore, we developed a web-browser based software to assist the ssDNA origami structure design. We generated a tiling arrangement of X-shape motifs, where those DNA motifs were connected into a periodic isogonal tiling consisting of rows of rectangles with vertical offsets to cover whole plane. Various shapes can be created by selecting desired modular building blocks on this pre-designed tiling map. After selecting desired modules to represent target structure, the next step is routing all the helices into one single strand. Given the fact that each click highlights one module and creates zero or two more ends, the total number of terminals of lines in any shape will be even. So looping any construction with 2N ends to single line needs N−1 linkages. Additionally, the spatial accessibility also need to be considered when linking neighboring ends. We enforced that the linkage only can be created between two adjacent ends in the same vertical column. Thus, appropriated adjustments for the length of terminals may be needed to facilitate effective linking.

Figure 7:
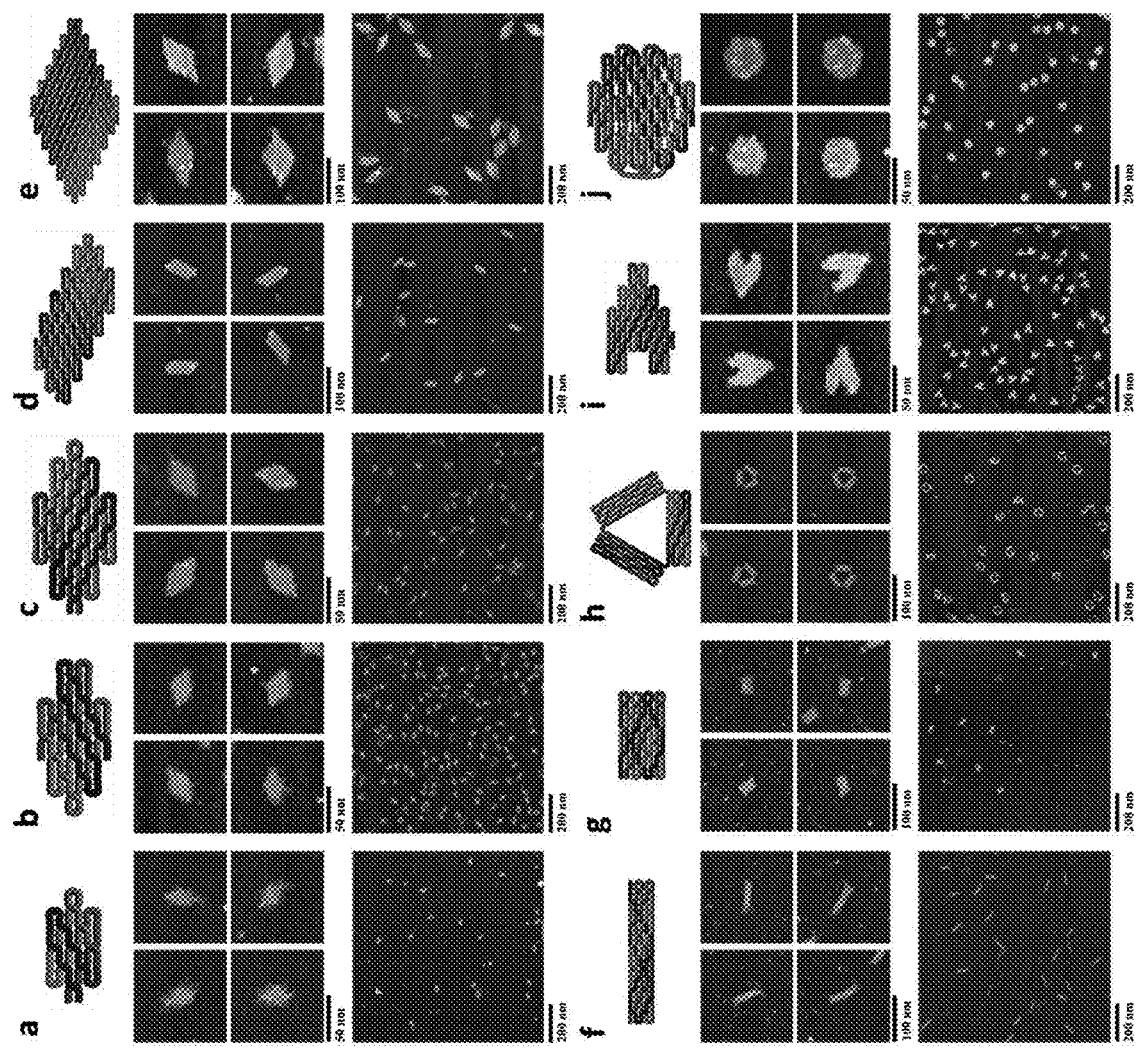
FIG. 7 presents DNA ssOrigami structures with 0 crossing number. a. 3×3 ssOrigami containing 966 nt. b. 4×4 ssOrigami containing 1,538 nt. c. 5×5 ssOrigami containing 2,238 nt. d. 5×10 ssOrigami containing 3,940 nt. e. 12×12 ssOrigami containing 10,682 nt. f. Strip shape ssOrigami (2,166 nt). g. Rectangle shape ssOrigami (1,884 nt). h. Triangle shape ssOrigami (3,439 nt). i. heart shape ssOrigami (2,849 nt). j. hexagon shape ssOrigami with patterned smile face containing 3,873 nt. Pipeline style models are shown in the top row. Zoomed-in and zoomed-out AFM images of diamond-shaped ssOrigami structures are shown in the middle and the bottom rows respectively.
Figure 8:
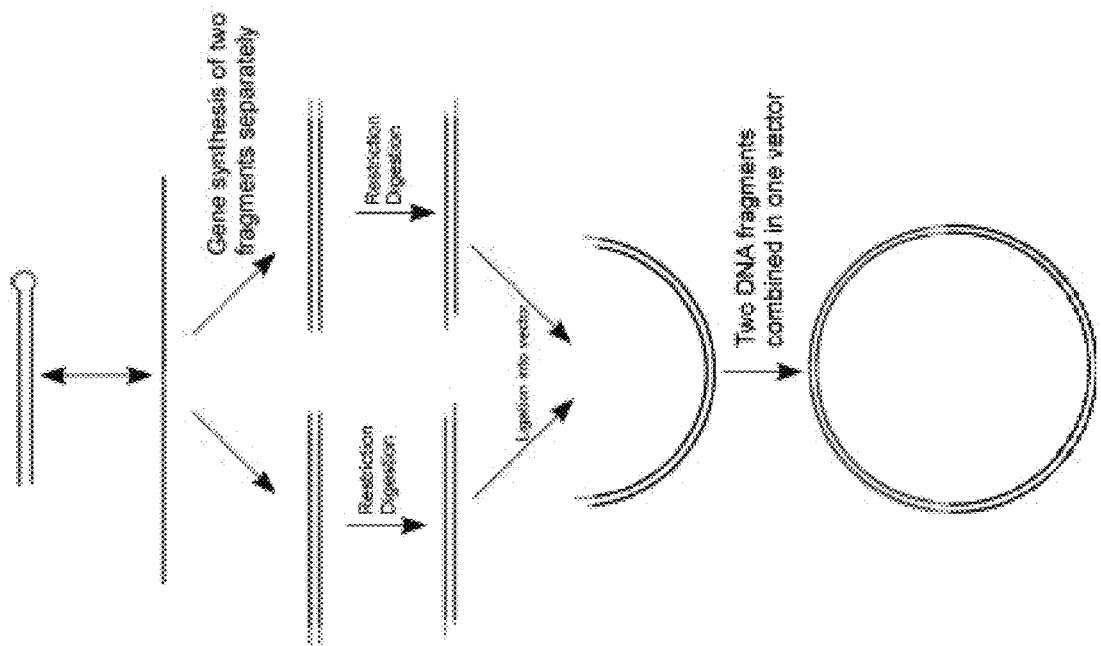
FIG. 8 is a schematic illustrating an exemplary method of gene synthesis and ssDNA origami sequence cloning.

Based on the design rule we develop, a set of ssDNA origami with no crossing number were created (FIG. 7).

Replicable ssRNA Origami Nanostructures

RNA, emerged as a unique polymeric material, has its own distinct advantages for nano-construction. Unlike DNA, RNA has its inherent architectural potential to form a variety of distinct interaction far beyond the Watson-Crick family. Numerous naturally existing 3D molecules and RNA building blocks/tiles at atomic resolution can be modified and have provided a versatile toolkit to build a variety of structures. In addition, functionalities associated with RNA molecules, such as catalysis, gene regulation and organizing proteins into large machineries, enable potential applications in biomedical and material sciences. However, it remains one of the grand challenges in RNA nanotechnology that rational designing objects with comparable size or complexity to natural RNA machines, or current highly sophisticated DNA nanostructures with heavy molecule weights.

We thus extended the concept of designing single-stranded replicable DNA origami nanostructures to a series of replicable ssRNA origami nanostructures. To synthesize long single-stranded RNA molecules, the DNA template with both T7 and T3 promoter sequences was first synthesized as two fragments similar to the ssDNA origami design. The two DNA fragments were ordered from Biobasic Inc. and cloned into pUC57 vector. The two fragments were then subcloned into the same and amplified in E. coli. The purified plasmids were then linearized by EcoRI and HindIII, and transcribed using T7 RNA polymerase or T3 RNA polymerase (New England Biolabs).

The X-shape motif can be modified from DNA to RNA by adjusting geometric parameters. Two key parameters we need to determine: how many bases for paranemic cohesion and how long for the stem of regular dsRNA. The first parameter determines the rigidity of the cohesive interaction. Based on 3D modeling of A-form helix, 8 or 3 bases were chosen as the internal length between two crossovers as the best geometrically fitting, angering with the reported simulation results. For the 8 bases cohesion, the total of $4^8=65536$ possibilities provides an adequate sequence space for the selection of unique complementarity. The 3 bases cohesion has $4^3=64$ possible combinations. The second parameter determines the flatness of final assembled structures of motifs. Given the 11 base pairs per turn of standard dsRNA, we assigned the inter-motif stems length. Two layouts of RNA motifs assembly were chose: one contains 8 bases paranemic cohesion and the other one contains 8 bases and 3 bases cohesion alternatively. The reason for skipping the design with 3 bases cohesion only is its weak interaction as well as the limitation of unique sequence combinations. After looping neighboring ends to form an ssRNA, appropriate sequences were assigned to the scaffold strand. The experimental results revealed the only successful formation for 8-bases design, indicating the 3-bases cohesion didn't provide sufficient binding or specific recognitions. Therefore, the 8-bases RNA motif were utilized as the modular building block in our software. The routing of ssRNA were converted into connecting all the X-shape blocks to form single path, which can be achieved by joining every two terminals of horizontal rows of target structure. After finalizing the geometry and routing ssRNA, a code representing the base pairing conditions will be generated as well as an initial raw RNA sequence. Our sequence optimization program will generate the final sequence automatically by inputting the code of base pairing.

Based on this design rule we developed, a set of ssRNA origami nanostructures were created with size up to 6.3 k, equivalent to the size of 28 S rRNA.

Bivalent Aptamer Selection

Aptamers are oligonucleotide molecules that bind to specific target molecules (e.g., proteins, sugars, drugs, etc.). Systematic evolution of ligands by exponential enrichment (SELEX) has been a very powerful strategy for developing DNA or RNA aptamers for interested target molecules. Theoretically aptamers binding to any epitopes on the same target molecule can be simultaneously evolved from a single selection process, however nearly all aptamers identified so far for any given target molecule are specific to just one epitope. Due to the fact that multivalent interactions will increase the binding affinity between aptamer and the target molecule, we proposed that we can evolve pairs of aptamers that bind to two different epitopes from rationally designed single stranded DNA nanostructures, which is enzymatically self-replicable to meet the requirements in SELEX.

A two-helix DNA nanostructure with paranemic crossovers was designed as the scaffold to support the two 20-mer random loops for aptamer selection. The total length of the library DNA was 145 nt, which included the 40-nt random sequences in the loop region and the constant sequences in the scaffold structure. Before selection, thrombin, the benchmark target protein with two established aptamers (TBA and HD22) that binds to two epitopes, was immobilized on the NHS-activated magnetic beads. In the first round of selection, DNA library with $1.5 \times 10^{15}$ molecules was incubated with thrombin coated magnetic beads in binding buffer (PBS supplemented with KCl, $MgCl_2$, BSA, yeast tRNA and tween-20) for 1 hour, and beads were then collected by magnetic stand and rinse with washing buffer three times. Bound DNA was eluted in water after heat denature, and then amplified by specific primers by PCR. The reverse primer had an extended sequence in 5' end joined by a chemical linker, so the two sequences generated during PCR have different lengths which can be separated by denaturing gel electrophoresis (PAGE) to recover the sense ssDNA for next round of selection. After three rounds of selection, counter selection with unmodified beads was introduced to remove unspecific aptamers that bind to beads. Selection stringency was gradually increasing by reducing DNA library and beads input, shortening library incubation time, extending counter selection time, and increasing washing volumes and times.

The forward primer was labeled with FITC dye, so the binding behavior of the dye labeled selected library can be monitored by FACS. 200 nM DNA library from $5^{th}$, $6^{th}$ or $7^{th}$ round of selection were incubated with unmodified magnetic beads or thrombin coated beads, and the fluorescence remaining on the beads were detected by FACS after rinse and resuspension in washing buffer. FACS results showed that after 7 rounds of selection the DNA library was enriched with aptamers with high affinity and good specificity, which suggested the end of the selection process.

Figures 11A, 11B, 11C:
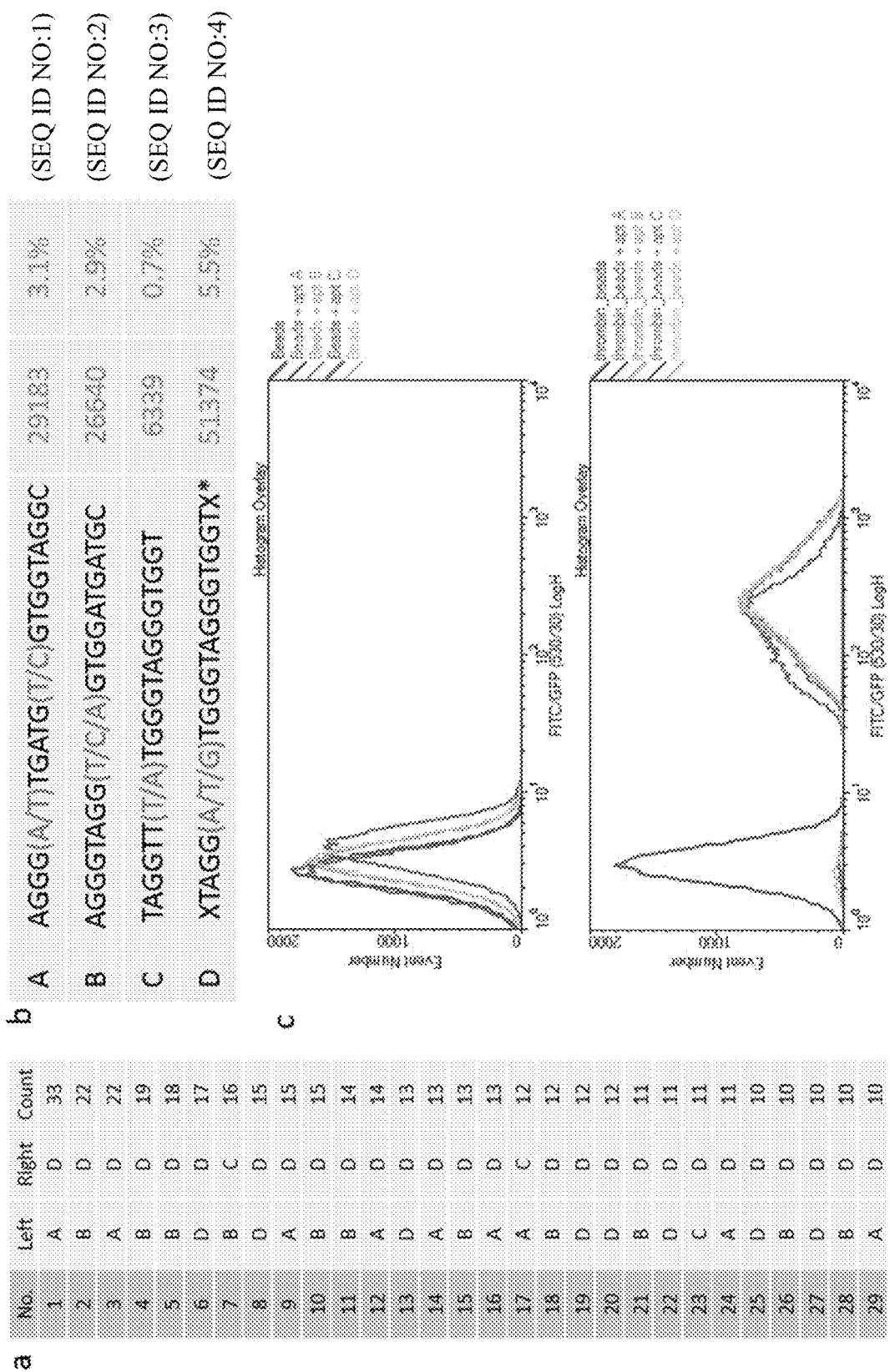
FIGS. 11A-11C demonstrates specific aptamer identification from sequencing results. A, 29 top ranked sequences and their combination between two loops. B, four potential monovalent aptamer families (A, B, C and D) and their copy number in the sequencing pool. C, FACS results for four representative aptamers A, B, C and D: aptamers with unmodified beads (top), and aptamers with thrombin coated beads (bottom).
Figure 12:
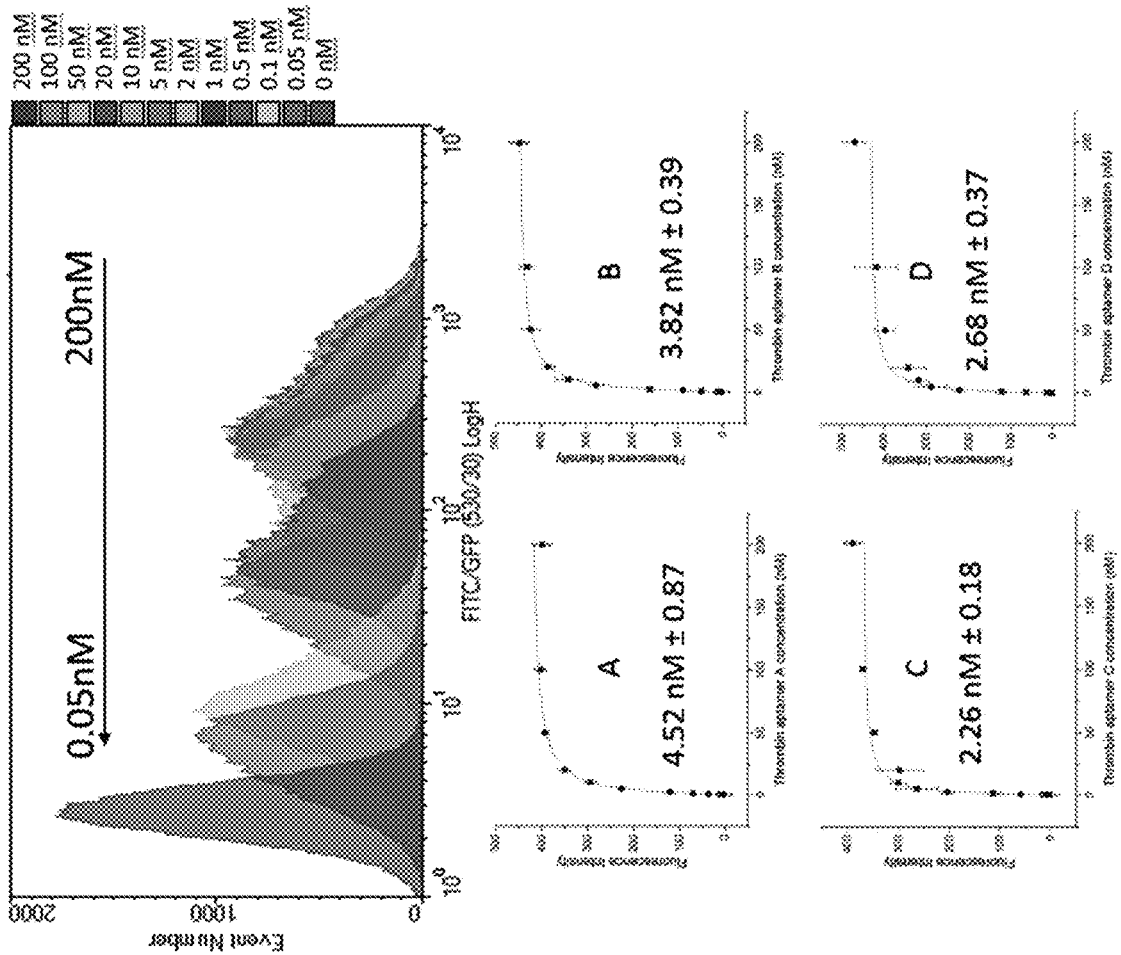
FIG. 12 presents aptamer Kd measurement. Aptamer concentrations were titrated from 0 nM to 200 nM and fluorescence was measured by FACS (left). The mean fluorescence value against aptamer concentration were plotted and curved to get the Kd values for each aptamer.

The selected DNA libraries were then sequenced by illumina high throughput sequencing. The sequencing results gave a very diverse DNA pool with a few sequences with relatively higher copy number. We used 10 copy number as the cutoff value to manually select 29 potential bivalent aptamers. Unexpectedly, all 29 sequences possessed a combination of two high-frequency sequences in the two loop region. These high-frequency sequences, or potential monovalent aptamers, were grouped by sequence similarities into four aptamer families referred to here as A, B, C and D (FIGS. 11A-11C). Representative high-frequency sequences from each family were tested for binding with thrombin coated beads by FACS. Results showed that all four aptamers bind with thrombin coated beads, and further tests with FACS by titrating aptamer concentrations showed that their Kd values are all around a few nanomolar (FIG. 12). For these assays, Kd was measured by FACS with serial dilutions of aptamers against a constant concentration of thrombin immobilized magnetic beads. Aptamers were labeled with FITC, so the mean fluorescence on the beads were plotted against individual aptamer concentrations and fitted with one-site saturation equations A=(Bmax*X)/(X+Kd). Kd value was determined using the equation.

Figure 14:
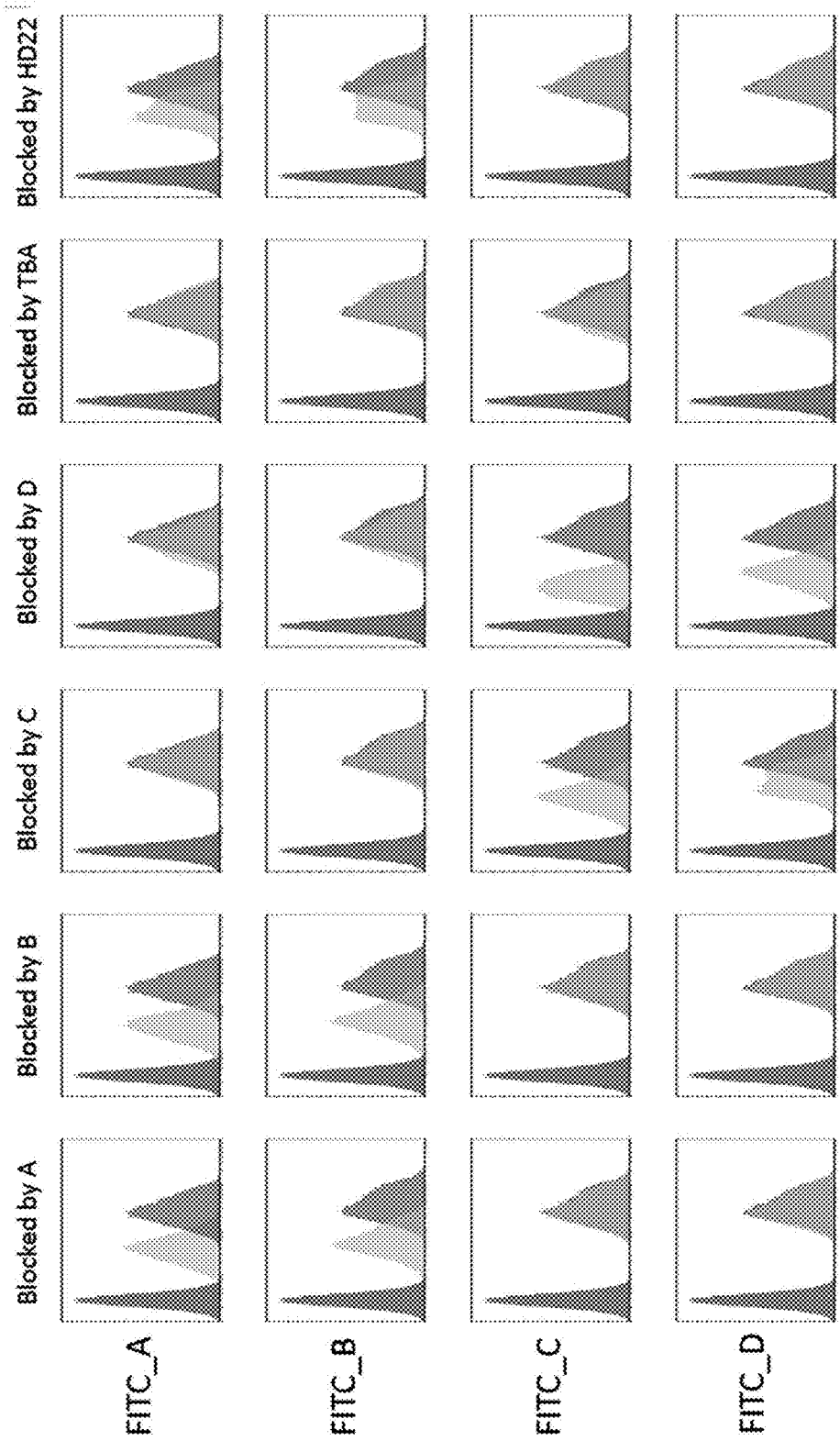
FIG. 14 presents an aptamer binding competition assay. Red, background signal from unmodified beads; Green, 10 nM aptamer binds with thrombin coated beads; Yellow, 10 nM aptamer binds with aptamer-blocked thrombin coated beads.

Since aptamers sharing the same or similar epitopes will compete each other for the binding site, we next sought to characterize the binding sites of these four aptamer families. For aptamer binding competition assays, thrombin-coated beads were pre-incubated with individual non-dye-labeled aptamers (200 nM each of A, B, C, D, TBA or HD22) to block specific binding sites. Next, fluorescence-labeled aptamers (10 nM) were added to the beads to compete with pre-incubated aptamers. If fluorescence decreased relative to the positive control (non-blocked beads with fluorescence labeled aptamer), the pre-incubated aptamer affected the binding of the fluorescence labeled aptamer, and the two aptamers likely share an overlapping binding site. If fluorescence was unchanged relative to positive controls, then the two aptamers likely bind to distinct epitopes on the protein. From the results (FIG. 14), A and B affected each other's binding, and both of them could be blocked by established aptamer HD22, suggesting that A and B might bind to the same epitope as HD22 (exosite II). C and D affected each other, but they were not affect by either TBA or HD22, indicating that C and D might bind to another epitope other than exosite I or II.

Figure 13:
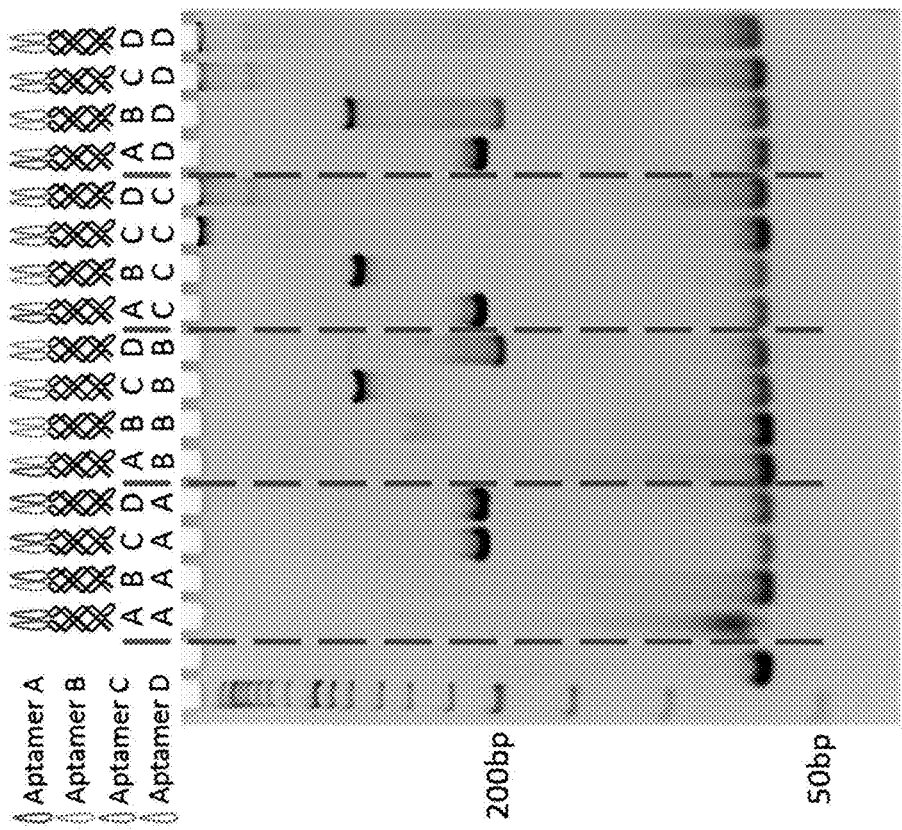
FIG. 13 presents a gel assay for bivalent aptamers. Left: bivalent aptamers with different combinations between aptamer A, B, C and D. 2 µM of DNA aptamers were incubated with 2 µM of thrombin. The first lane is the 2 µM DNA control without thrombin. Right: representative bivalent aptamer with hetero-binders (A,D) and homo-binders (C,D). 20 nM of the bivalent aptamers were incubated with different concentrations. The ratio between bivalent aptamer to thrombin vary from 1:0 to 1.

To characterize the bivalent aptamer, the four aptamers were paired and reconstructed into the 2-helix nanostructure in the positions of the two loops. The bivalent aptamer binding capacity was analyzed by the gel shift assay (FIG. 13). For this assay, varying concentrations of thrombin (0.1 nM to 12.8 nM) were incubated with bivalent aptamer AD (0.1 nM) and subjected with gel assay to check the mobility shift. From the gel, 0.1 nM thrombin is sufficient to bind to more than half of the aptamers, meaning that the Kd value for bivalent aptamer is lower than 100 pM. The results suggest that bivalent aptamers with combinations between hetero-binders (two aptamers that bind with two epitopes) show strong binding with thrombin with clear upper bands; while bivalent aptamers with aptamers that bind with the same epitope have relatively weaker binding and are more likely to dissociate when migrating through the gel.

Figure 15:
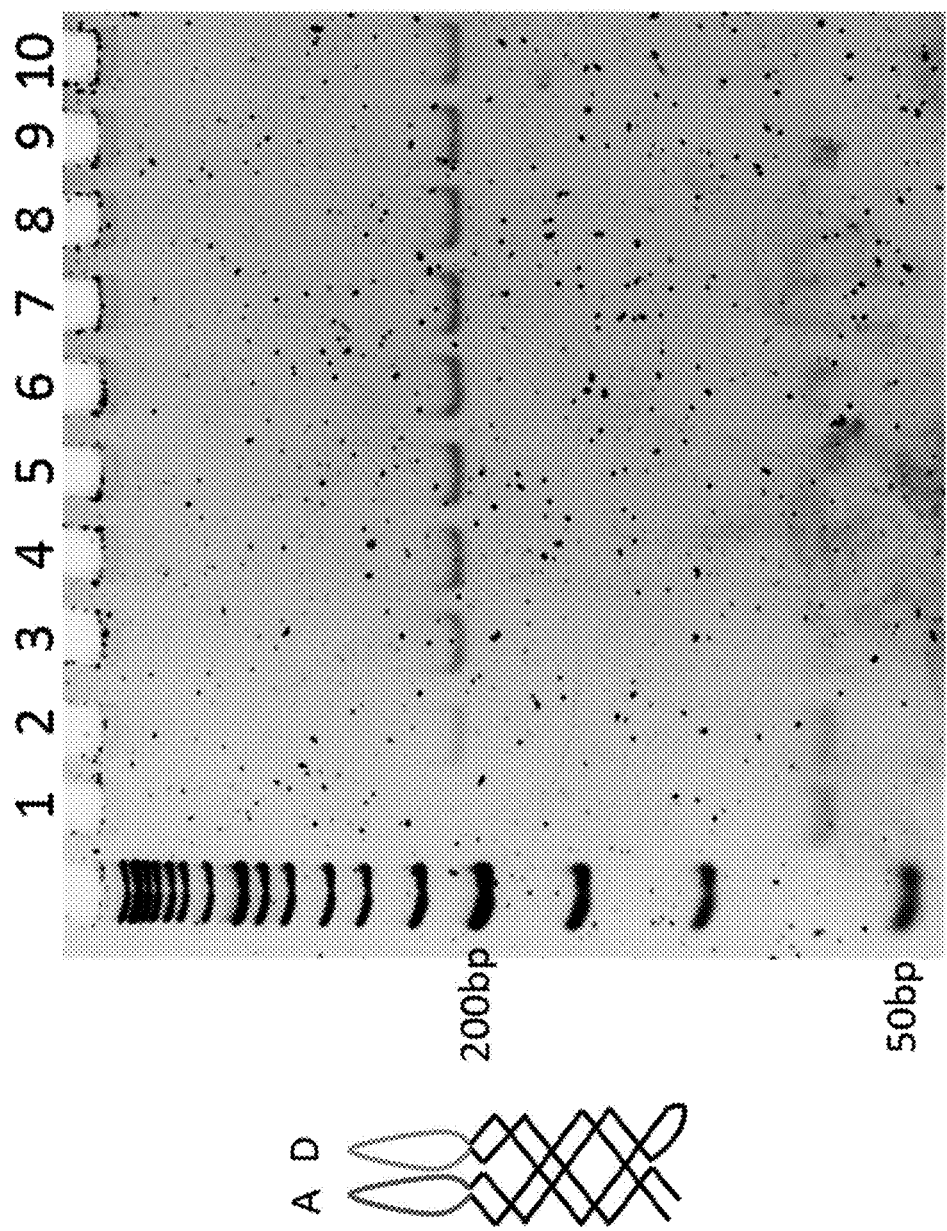
FIG. 15 demonstrates thrombin with varying concentrations titrated against 1 nM of bivalent aptamer AD. The concentration of thrombin from lane 1 to 10 is: 0 nM, 0.5 nM, 1 nM, 1.5 nM, 2 nM, 3 nM, 4 nM, 8 nM, 16 nM.

The bivalent aptamer AD with aptamer A as the right loop and D as the left loop is the most abundant combination in the selected pool. So we further tested the binding between AD and thrombin by titrating thrombin concentration against 1 nM of the aptamer. The result shows that the bivalent aptamer has very strong binding with thrombin even at very low concentrations (FIG. 15).

I claim:

1. A method for directed evolution of multivalent aptamers, the method comprising
   - (a1) linking by ligating a random library of nucleic acid sequences for aptamer selection to a defined single-stranded DNA (ssDNA) or RNA origami nano structure,
   - (a2) forming the defined single-stranded DNA (ssDNA) or RNA origami nanostructure into two random loop sequences by thermal annealing to form a scaffold-linked library;
   - (b) immobilizing a benchmark target polypeptide comprising one or more epitopes on a bead;
   - (c) contacting benchmark polypeptide-coated beads to the scaffold-linked library;
   - (d) recovering the contacted beads;
   - (e) eluting bound nucleic acid sequences linked by ligation to said defined single-stranded DNA (ssDNA) or RNA origami nanostructure sequence from the contacted beads;
   - (f) amplifying by in vitro PCR the eluted nucleic acid sequences linked by ligation to said defined single-stranded DNA (ssDNA) or RNA origami nanostructure sequence using a forward primer and a reverse primer, wherein the reverse primer has an extended sequence to generate amplification products of different nucleic acid lengths;
   - (g) separating the amplification products on a denaturing gel; and
   - (h) recovering sense single-stranded DNA (ssDNA) for one or more subsequent rounds of directed evolution,
   wherein the defined single-stranded DNA (ssDNA) or RNA origami nanostructure comprises a plurality of paranemic crossovers,
   wherein each member of the scaffold-linked library consists of one contiguous single strand of nucleic acids, and
   wherein the benchmark target polypeptide is a polypeptide to which the multivalent aptamers will have binding affinity of less than 100 pM (picomolar).

2. The method of claim 1, wherein the random library has a total length of about 120 nucleotides to about 180 nucleotides.

3. The method of claim 1, wherein the nucleic acid origami nanostructure is a Y-shaped ssDNA or ssRNA origami nanostructure.

4. The method of claim 1, wherein the bead is a magnetic bead.

5. The method of claim 1, wherein the sequences of the two random loop sequences are the same.

6. The method of claim 1, wherein the sequences of the two random loop sequences are different.

7. The method of claim 6, wherein the target polypeptide comprises two or more epitopes, and the sequences of the different two random loop sequences bind to the two or more epitopes of the target polypeptide.

8. The method of claim 1, wherein the two random loop sequences are independently from 10 to 20 nucleotides in length.

9. The method of claim 8, wherein the two random loop sequences are each 20 nucleotides in length.

10. The method of claim 1, wherein the generated amplification products of different nucleic acid lengths are detected using a method selected from gel electrophoresis or next-generation DNA sequencing.

11. The method of claim 1, wherein the defined single-stranded DNA (ssDNA) or RNA origami nanostructure comprises two anti-parallel double helices.

12. The method of claim 1, wherein the nucleic acids length of the defined single-stranded DNA (ssDNA) or RNA origami nanostructure is up to 6.3 kilobases.

13. The method of claim 1, wherein the benchmark target polypeptide is thrombin.

14. The method of claim 1, wherein said subsequent one or more rounds of directed evolution is performed with increasing stringency.

15. The method of claim 14, wherein the increasing stringency is performed using a method selected from: reducing the concentration of random library of nucleic acid sequences for aptamer selection linked to a defined single-stranded DNA (ssDNA) or RNA origami nanostructure DNA, reducing the concentration of polypeptide beads, and contacting benchmark polypeptide-coated beads to the scaffold-linked library for shorter time than was performed in a previous round of directed evolution.

16. The method of claim 1, wherein the defined single-stranded DNA (ssDNA) or RNA origami nanostructure comprises at least two paranemic crossovers.

17. The method of claim 16, wherein the paranemic crossovers are separated by at least 8 base pairs.

18. The method of claim 1, wherein the defined single-stranded DNA (ssDNA) or RNA origami nanostructure comprises at least two paranemic crossover motifs, with each paranemic crossover motif further comprising one of the said random loop sequences.

19. The method of claim 1, wherein the defined single-stranded DNA (ssDNA) or RNA origami nanostructure does not comprise a sticky end.

20. The method of claim 1, wherein seven or fewer rounds of directed evolution are performed.

* * * * *